United States Patent
Yomo et al.

(10) Patent No.: US 9,862,942 B2
(45) Date of Patent: Jan. 9, 2018

(54) IN VITRO MEMBRANE PROTEIN MOLECULAR EVOLUTIONARY ENGINEERING TECHNIQUE

(71) Applicant: Japan Science and Technology Agency, Saitama (JP)

(72) Inventors: Tetsuya Yomo, Osaka (JP); Tomoaki Matsuura, Osaka (JP); Haruka Soga, Osaka (JP); Hajime Watanabe, Osaka (JP); Satoshi Fujii, Osaka (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 403 days.

(21) Appl. No.: 14/411,892

(22) PCT Filed: Jun. 17, 2013

(86) PCT No.: PCT/JP2013/003767
§ 371 (c)(1),
(2) Date: Dec. 29, 2014

(87) PCT Pub. No.: WO2014/002424
PCT Pub. Date: Jan. 3, 2014

(65) Prior Publication Data
US 2015/0176004 A1    Jun. 25, 2015

(30) Foreign Application Priority Data
Jun. 28, 2012 (JP) ................................. 2012-145795

(51) Int. Cl.
C12N 15/11 (2006.01)
C12P 21/02 (2006.01)
C12N 15/10 (2006.01)
C12Q 1/68 (2006.01)

(52) U.S. Cl.
CPC ............ *C12N 15/11* (2013.01); *C12N 15/102* (2013.01); *C12N 15/1034* (2013.01); *C12P 21/02* (2013.01); *C12Q 1/686* (2013.01)

(58) Field of Classification Search
None
See application file for complete search history.

(56) References Cited

FOREIGN PATENT DOCUMENTS

JP    2012-210170 A    11/2012

OTHER PUBLICATIONS

Kalmbach et al (2007 JMB 371:639-48).*
Ma et al (1996 Methods: A companion to Methods in Enzymology vol. 10 pp. 273-278).*
Wang et al (1989 PNAS 86:9717-21).*
English Translation of Soga et al., "Construction of an in vitro gene screening system for membrane proteins," *Abstracts of the Annual Meeting of the Society for Biotechnology* 64:194, 2012.
Hovijitra et al., "Cell-Free Synthesis of Functional Aquaporin Z in Synthetic Liposomes," *Biotechnology and Bioengineering* 104(1):40-49, 2009.
International Search Report, dated Sep. 17, 2013, for International Application No. PCT/JP2013/003767, 5 pages.
Kuruma, "Question 7: Biosynthesis of Phosphatidic Acid in Liposome Compartments—Toward the Self-Reproduction of Minimal Cells," *Orig. Life Evol. Biosph.* 37:409-413, 2007.
Nishikawa et al., "Quantitative Analysis of Gene Screening System using Unilamellar Lipsomes and Fluorescence Activated Cell Sorter," *Polymer Preprints* 60(2):4773-4774, 2011. (English Abstract Only).
Nishikawa et al., "Selection of Active Glucuronidase Variants Using Gene Screening System Based on Giant Unilamellar Liposomes and Fluorescence Activated Cell Sorter," *Polymer Preprints* 61(1):1604, 2012. (English Abstract Only).
Nishikawa et al., "Construction of a Gene Screening System Using Giant Unilamellar Liposomes and a Fluorescence-Activated Cell Sorter," *Analytical Chemistry* 84:5017-5024, 2012.
Nishkawa et al., "Directed Evolution of Proteins through In Vitro Protein Synthesis in Liposomes," *Journal of Nucleic Acids* 2012:923214, 11 pages.
Noireaux et al., "A vesicle bioreactor as a step toward an artificial cell assembly," *PNAS* 101(51):17669-17674, 2004.
Ohtsuka et al., "Synthesis and in situ insertion of a site-specific fluorescently labeled membrane protein into cell-sized liposomes," *Analytical Biology* 418:97-101, 2011.
Soga et al., "Construction of an in vitro gene screening system for membrane proteins," *Abstracts of the Annual Meeting of the Society for Biotechnology* 64:194, 2012.
Carlson et al., "Cell-free protein synthesis: Applications come of age," *Biotechnol Adv* (2011), doi:10.1016/j.biotechadv.2011.09.016, 10 pages.
Fujii et al., "Liposome display for in vitro selection and evolution of membrane proteins," *Nature Protocols* 9(7):1578-1591, 2014.
Nishikawa et al., "Quantitative screening system of β-glucuronidase genes using unilamellar liposomes and cell sorter," *Abstracts of Papers American Chemical Society* 241:465, 2011, 1 page.
Nozawa et al., "Production and partial purification of membrane proteins using a liposome-supplemented wheat cell-free translation system," *BMC Biotechnology* 11, 2011, 10 pages.

* cited by examiner

*Primary Examiner* — Christopher M Gross
(74) *Attorney, Agent, or Firm* — Seed IP Law Group LLP

(57) ABSTRACT

The objective of the present invention is to improve the efficiency of screening/selection of a membrane protein in molecular evolutionary engineering (for example, an enzyme evolutionary method).
The above-described objective is achieved by providing a unilamellar liposome comprising:
(a) a DNA comprising a promoter sequence, a translational initiation sequence, and a sequence encoding a membrane protein;
(b) an RNA polymerase;
(c) a ribonucleotide; and
(d) a cell-free protein synthesis system. In one aspect of the present invention, the membrane protein is a transporter, and the unilamellar liposome further comprises
(e) a factor that binds to a ligand transported by the membrane protein.

11 Claims, 3 Drawing Sheets

[Fig. 1]
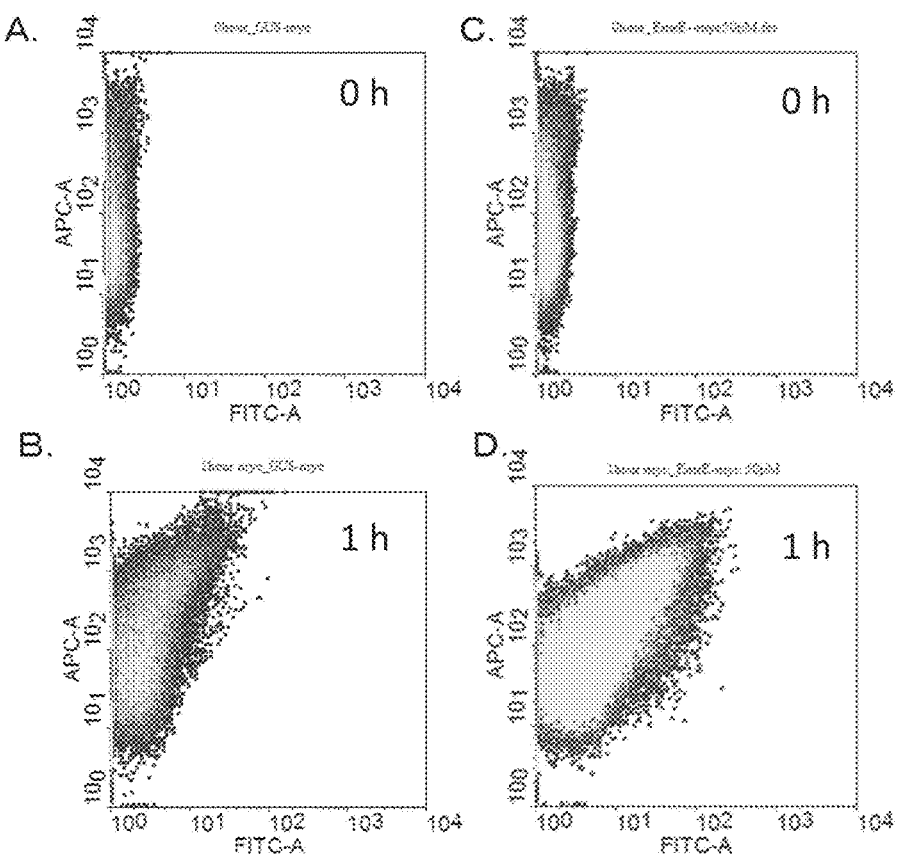
[Fig. 2]
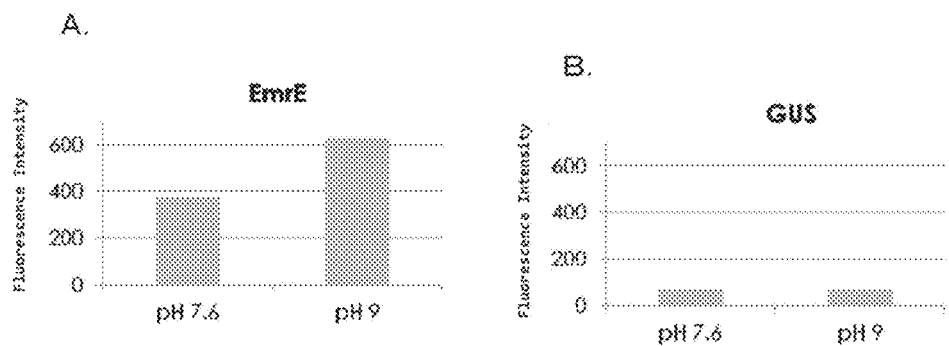

[Fig. 3]
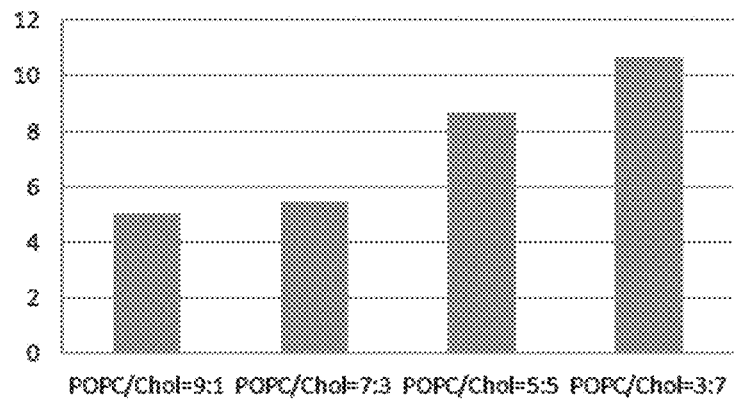
[Fig. 4]
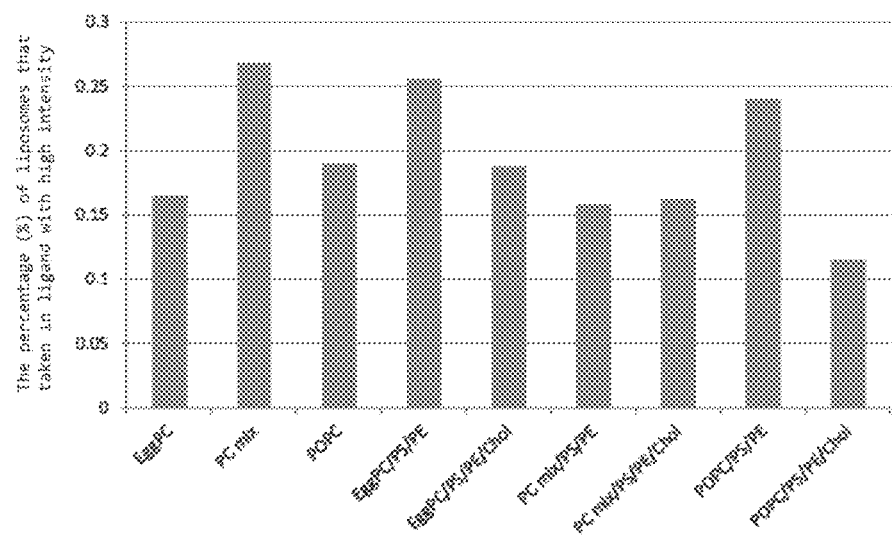

[Fig. 5]
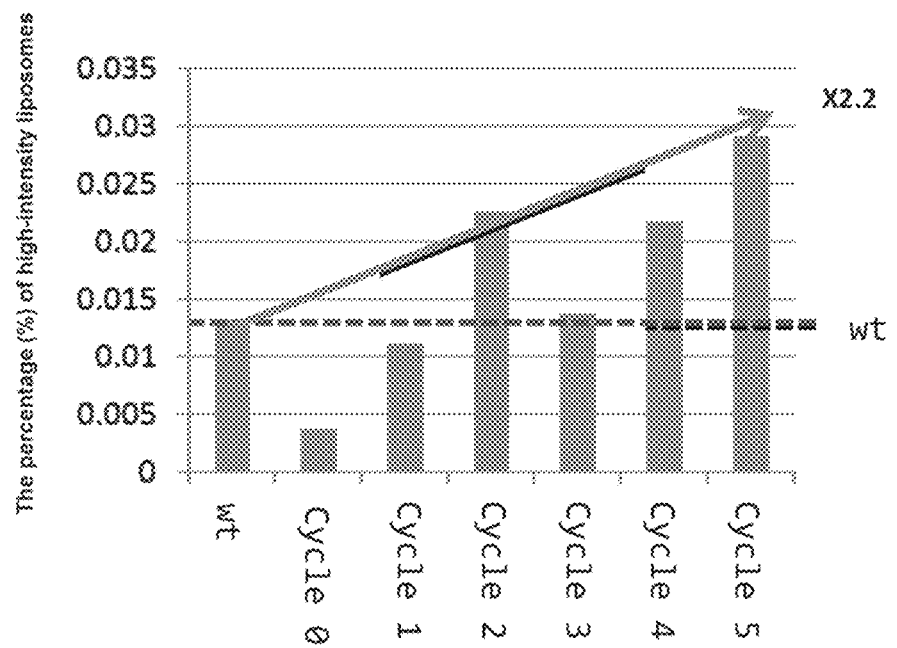

```
SEQUENCE LISTING

<160> NUMBER OF SEQ ID NOS: 9

<210> SEQ ID NO 1
<211> LENGTH: 414
<212> TYPE: DNA
<213> ORGANISM: Artificial Sequence
<220> FEATURE:
<223> OTHER INFORMATION: EmrE-myc-his
<220> FEATURE:
<221> NAME/KEY: CDS
<222> LOCATION: (1)..(414)

<400> SEQUENCE: 1 atg aac cct tat att tat ctt ggt ggt gca ata ctt gca gag gtc att      48
Met Asn Pro Tyr Ile Tyr Leu Gly Gly Ala Ile Leu Ala Glu Val Ile
1               5                   10                  15
```

```
ggt aca acc tta atg aag ttt tca gaa ggt ttt aca cgg tta tgg cca      96
Gly Thr Thr Leu Met Lys Phe Ser Glu Gly Phe Thr Arg Leu Trp Pro
         20                  25                  30 tct gtt ggt aca att att tgt tat tgt gca tca ttc tgg tta tta gct     144
Ser Val Gly Thr Ile Ile Cys Tyr Cys Ala Ser Phe Trp Leu Leu Ala
         35                  40                  45 cag acg ctg gct tat att cct aca ggg att gct tat gct atc tgg tca     192
Gln Thr Leu Ala Tyr Ile Pro Thr Gly Ile Ala Tyr Ala Ile Trp Ser
50                   55                  60 gga gtc ggt att gtc ctg att agc tta ctg tca tgg gga ttt ttc ggc     240
Gly Val Gly Ile Val Leu Ile Ser Leu Leu Ser Trp Gly Phe Phe Gly
65                  70                  75                  80 caa cgg ctg gac ctg cca gcc att ata ggc atg atg ttg att tgt gcc     288
Gln Arg Leu Asp Leu Pro Ala Ile Ile Gly Met Met Leu Ile Cys Ala
             85                  90                  95 ggt gtg ttg att att aat tta ttg tca cga agc aca cca cat gaa ttt     336
Gly Val Leu Ile Ile Asn Leu Leu Ser Arg Ser Thr Pro His Glu Phe
            100                 105                 110 gag gca tat gtt gag caa aaa tta ata agt gaa gaa gat ttg aat agc     384
Glu Ala Tyr Val Glu Gln Lys Leu Ile Ser Glu Glu Asp Leu Asn Ser
        115                 120                 125 gct gta gac cat cac cat cac cat cac taa                             414
Ala Val Asp His His His His His His
        130                 135

<210> SEQ ID NO 2
<211> LENGTH: 137
<212> TYPE: PRT
<213> ORGANISM: Artificial Sequence
<220> FEATURE:
<223> OTHER INFORMATION: Synthetic Construct

<400> SEQUENCE: 2

Met Asn Pro Tyr Ile Tyr Leu Gly Gly Ala Ile Leu Ala Glu Val Ile
1               5                  10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His Glu Phe
            100                 105                 110

Glu Ala Tyr Val Glu Gln Lys Leu Ile Ser Glu Glu Asp Leu Asn Ser
        115                 120                 125

Ala Val Asp His His His His His His
    130                 135

<210> SEQ ID NO 3
<211> LENGTH: 2406
<212> TYPE: DNA
<213> ORGANISM: Escherichia coli
<220> FEATURE:
<221> NAME/KEY: CDS
<222> LOCATION: (1)..(2406)
```

-continued

<400> SEQUENCE: 3

```
tta cgt cct gta gaa acc cca acc cgt gaa atc aaa aaa ctc gac ggc       48
Leu Arg Pro Val Glu Thr Pro Thr Arg Glu Ile Lys Lys Leu Asp Gly
 1               5                  10                  15 ctg tgg gca ttc agt ctg gat cgc gaa aac tgt gga att gat cag cgt       96
Leu Trp Ala Phe Ser Leu Asp Arg Glu Asn Cys Gly Ile Asp Gln Arg
             20                  25                  30 tgg tgg gaa agc gcg tta caa gaa agc cgg gca att gct gtg cca ggc      144
Trp Trp Glu Ser Ala Leu Gln Glu Ser Arg Ala Ile Ala Val Pro Gly
         35                  40                  45 agt ttt aac gat cag ttc gcc gat gca gat att cgt aat tat gcg ggc      192
Ser Phe Asn Asp Gln Phe Ala Asp Ala Asp Ile Arg Asn Tyr Ala Gly
     50                  55                  60 aac gtc tgg tat cag cgc gaa gtc ttt ata ccg aaa ggt tgg gca ggc      240
Asn Val Trp Tyr Gln Arg Glu Val Phe Ile Pro Lys Gly Trp Ala Gly
 65                  70                  75                  80 cag cgt atc gtg ctg cgt ttc gat gcg gtc act cat tac ggc aaa gtg      288
Gln Arg Ile Val Leu Arg Phe Asp Ala Val Thr His Tyr Gly Lys Val
                 85                  90                  95 tgg gtc aat aat cag gaa gtg atg gag cat cag ggc ggc tat acg cca      336
Trp Val Asn Asn Gln Glu Val Met Glu His Gln Gly Gly Tyr Thr Pro
            100                 105                 110 ttt gaa gcc gat gtc acg ccg tat gtt att gcc ggg aaa agt gta cgt      384
Phe Glu Ala Asp Val Thr Pro Tyr Val Ile Ala Gly Lys Ser Val Arg
        115                 120                 125 atc acc gtt tgt gtg aac aac gaa ctg aac tgg cag act atc ccg ccg      432
Ile Thr Val Cys Val Asn Asn Glu Leu Asn Trp Gln Thr Ile Pro Pro
    130                 135                 140 gga atg gtg att acc gac gaa aac ggc aag aaa aag cag tct tac ttc      480
Gly Met Val Ile Thr Asp Glu Asn Gly Lys Lys Lys Gln Ser Tyr Phe
145                 150                 155                 160 cat gat ttc ttt aac tat gcc ggg atc cat cgc agc gta atg ctc tac      528
His Asp Phe Phe Asn Tyr Ala Gly Ile His Arg Ser Val Met Leu Tyr
                165                 170                 175 acc acg ccg aac acc tgg gtc gac gat atc acc gtg gtg acg cat gtc      576
Thr Thr Pro Asn Thr Trp Val Asp Asp Ile Thr Val Val Thr His Val
            180                 185                 190 gcg caa gac tgt aac cac gcg tct gtt gac tgg cag gtg gtg gcc aat      624
Ala Gln Asp Cys Asn His Ala Ser Val Asp Trp Gln Val Val Ala Asn
        195                 200                 205 ggt gat gtc agc gtt gaa ctg cgt gat gcg gat caa cag gtg gtt gca      672
Gly Asp Val Ser Val Glu Leu Arg Asp Ala Asp Gln Gln Val Val Ala
    210                 215                 220 act gga caa ggc act agc ggg act ttg caa gtg gtg aat ccg cac ctc      720
Thr Gly Gln Gly Thr Ser Gly Thr Leu Gln Val Val Asn Pro His Leu
225                 230                 235                 240 tgg caa ccg ggt gaa ggt tat ctc tat gaa ctg tgc gtc aca gcc aaa      768
Trp Gln Pro Gly Glu Gly Tyr Leu Tyr Glu Leu Cys Val Thr Ala Lys
                245                 250                 255 agc cag aca gag tgt gat atc tac ccg ctt cgc gtc ggc atc cgg tca      816
Ser Gln Thr Glu Cys Asp Ile Tyr Pro Leu Arg Val Gly Ile Arg Ser
            260                 265                 270 gtg gca gtg aag ggc gaa cag ttc ctg att aac cac aaa ccg ttc tac      864
Val Ala Val Lys Gly Glu Gln Phe Leu Ile Asn His Lys Pro Phe Tyr
        275                 280                 285 ttt act ggc ttt ggt cgt cat gaa gat gcg gac ttg cgt ggc aaa gga      912
Phe Thr Gly Phe Gly Arg His Glu Asp Ala Asp Leu Arg Gly Lys Gly
    290                 295                 300
```

-continued

| | | |
|---|---|---|
| ttc gat aac gtg ctg atg gtg cac gac cac gca tta atg gac tgg att<br>Phe Asp Asn Val Leu Met Val His Asp His Ala Leu Met Asp Trp Ile<br>305                     310                     315                     320 | 960 |
| ggg gcc aac tcc tac cgt acc tcg cat tac cct tac gct gaa gag atg<br>Gly Ala Asn Ser Tyr Arg Thr Ser His Tyr Pro Tyr Ala Glu Glu Met<br>                     325                     330                     335 | 1008 |
| ctc gac tgg gca gat gaa cat ggc atc gtg gtg att gat gaa act gct<br>Leu Asp Trp Ala Asp Glu His Gly Ile Val Val Ile Asp Glu Thr Ala<br>                     340                     345                     350 | 1056 |
| gct gtc ggc ttt aac ctc tct tta ggc att ggt ttc gaa gcg ggc aac<br>Ala Val Gly Phe Asn Leu Ser Leu Gly Ile Gly Phe Glu Ala Gly Asn<br>            355                     360                     365 | 1104 |
| aag ccg aaa gaa ctg tac agc gaa gag gca gtc aac ggg gaa act cag<br>Lys Pro Lys Glu Leu Tyr Ser Glu Glu Ala Val Asn Gly Glu Thr Gln<br>370                     375                     380 | 1152 |
| caa gcg cac tta cag gcg att aaa gag ctg ata gcg cgt gac aaa aac<br>Gln Ala His Leu Gln Ala Ile Lys Glu Leu Ile Ala Arg Asp Lys Asn<br>385                     390                     395                     400 | 1200 |
| cac cca agc gtg gtg atg tgg agt att gcc aac gaa ccg gat acc cgt<br>His Pro Ser Val Val Met Trp Ser Ile Ala Asn Glu Pro Asp Thr Arg<br>                                   405                     410                     415 | 1248 |
| ccg caa ggt gca cgg gaa tat ttc gcg cca ctg gcg gaa gca acg cgt<br>Pro Gln Gly Ala Arg Glu Tyr Phe Ala Pro Leu Ala Glu Ala Thr Arg<br>                     420                     425                     430 | 1296 |
| aaa ctc gac ccg acg cgt ccg atc acc tgc gtc aat gta atg ttc tgc<br>Lys Leu Asp Pro Thr Arg Pro Ile Thr Cys Val Asn Val Met Phe Cys<br>                     435                     440                     445 | 1344 |
| gac gct cac acc gat acc atc agc gat ctc ttt gat gtg ctg tgc ctg<br>Asp Ala His Thr Asp Thr Ile Ser Asp Leu Phe Asp Val Leu Cys Leu<br>450                     455                     460 | 1392 |
| aac cgt tat tac gga tgg tat gtc caa agc ggc gat ttg gaa acg gca<br>Asn Arg Tyr Tyr Gly Trp Tyr Val Gln Ser Gly Asp Leu Glu Thr Ala<br>465                     470                     475                     480 | 1440 |
| gag aag gta ctg gaa aaa gaa ctt ctg gcc tgg cag gag aaa ctg cat<br>Glu Lys Val Leu Glu Lys Glu Leu Leu Ala Trp Gln Glu Lys Leu His<br>                                   485                     490                     495 | 1488 |
| cag ccg att atc atc acc gaa tac ggc gtg gat acg tta gcc ggg ctg<br>Gln Pro Ile Ile Ile Thr Glu Tyr Gly Val Asp Thr Leu Ala Gly Leu<br>                     500                     505                     510 | 1536 |
| cac tca atg tac acc gac atg tgg agt gaa gag tat cag tgt gca tgg<br>His Ser Met Tyr Thr Asp Met Trp Ser Glu Glu Tyr Gln Cys Ala Trp<br>            515                     520                     525 | 1584 |
| ctg gat atg tat cac cgc gtc ttt gat cgc gtc agc gcc gtc gtc ggt<br>Leu Asp Met Tyr His Arg Val Phe Asp Arg Val Ser Ala Val Val Gly<br>530                     535                     540 | 1632 |
| gaa cag gta tgg aat ttc gcc gat ttt gcg acc tcg caa ggc ata ttg<br>Glu Gln Val Trp Asn Phe Ala Asp Phe Ala Thr Ser Gln Gly Ile Leu<br>545                     550                     555                     560 | 1680 |
| cgc gtt ggc ggt aac aag aaa ggg atc ttc act cgc gac cgc aaa ccg<br>Arg Val Gly Gly Asn Lys Lys Gly Ile Phe Thr Arg Asp Arg Lys Pro<br>                     565                     570                     575 | 1728 |
| aag tcg gcg gct ttt ctg ctg caa aaa cgc tgg act ggc atg aac ttc<br>Lys Ser Ala Ala Phe Leu Leu Gln Lys Arg Trp Thr Gly Met Asn Phe<br>            580                     585                     590 | 1776 |
| ggt gaa aaa ccg cag cag gga ggc aaa caa ggc cta tgc ggc cgc aag<br>Gly Glu Lys Pro Gln Gln Gly Gly Lys Gln Gly Leu Cys Gly Arg Lys<br>                 595                     600                     605 | 1824 |
| ctt atg gac aaa gat tgc gaa atg aaa cgt acc acc ctg gat agc ccg<br>Leu Met Asp Lys Asp Cys Glu Met Lys Arg Thr Thr Leu Asp Ser Pro<br>610                     615                     620 | 1872 |

```
ctg ggc aaa ctg gaa ctg agc ggc tgc gaa cag ggc ctg cat gaa att    1920
Leu Gly Lys Leu Glu Leu Ser Gly Cys Glu Gln Gly Leu His Glu Ile
625                 630                 635                 640 aaa ctg ctg ggt aaa ggc acc agc gcg gcc gat gcg gtt gaa gtt ccg    1968
Lys Leu Leu Gly Lys Gly Thr Ser Ala Ala Asp Ala Val Glu Val Pro
            645                 650                 655 gcc ccg gcc gcc gtg ctg ggt ggt ccg gaa ccg ctg atg cag gcg acc    2016
Ala Pro Ala Ala Val Leu Gly Gly Pro Glu Pro Leu Met Gln Ala Thr
            660                 665                 670 gcg tgg ctg aac gcg tat ttt cat cag ccg gaa gcg att gaa gaa ttt    2064
Ala Trp Leu Asn Ala Tyr Phe His Gln Pro Glu Ala Ile Glu Glu Phe
            675                 680                 685 ccg gtt ccg gcg ctg cat cat ccg gtg ttt cag cag gag agc ttt acc    2112
Pro Val Pro Ala Leu His His Pro Val Phe Gln Gln Glu Ser Phe Thr
            690                 695                 700 cgt cag gtg ctg tgg aaa ctg ctg aaa gtg gtt aaa ttt ggc gaa gtg    2160
Arg Gln Val Leu Trp Lys Leu Leu Lys Val Val Lys Phe Gly Glu Val
705                 710                 715                 720 att agc tat cag cag ctg gcc gcc ctg gcg ggt aat ccg gcg gcc acc    2208
Ile Ser Tyr Gln Gln Leu Ala Ala Leu Ala Gly Asn Pro Ala Ala Thr
                725                 730                 735 gcc gcc gtt aaa acc gcg ctg agc ggt aac ccg gtg ccg att ctg att    2256
Ala Ala Val Lys Thr Ala Leu Ser Gly Asn Pro Val Pro Ile Leu Ile
                740                 745                 750 ccg tgc cat cgt gtg gtt agc tct agc ggt gcg gtt ggc ggt tat gaa    2304
Pro Cys His Arg Val Val Ser Ser Ser Gly Ala Val Gly Gly Tyr Glu
                755                 760                 765 ggt ggt ctg gcg gtg aaa gag tgg ctg ctg gcc cat gaa ggt cat cgt    2352
Gly Gly Leu Ala Val Lys Glu Trp Leu Leu Ala His Glu Gly His Arg
770                 775                 780 ctg ggt aaa ccg ggt ctg gga cct gca ggt ata ggg cac cac cac cac    2400
Leu Gly Lys Pro Gly Leu Gly Pro Ala Gly Ile Gly His His His His
785                 790                 795                 800 cac cac                                                            2406
His His

<210> SEQ ID NO 4
<211> LENGTH: 802
<212> TYPE: PRT
<213> ORGANISM: Escherichia coli

<400> SEQUENCE: 4

Leu Arg Pro Val Glu Thr Pro Thr Arg Glu Ile Lys Lys Leu Asp Gly
1               5                   10                  15

Leu Trp Ala Phe Ser Leu Asp Arg Glu Asn Cys Gly Ile Asp Gln Arg
            20                  25                  30

Trp Trp Glu Ser Ala Leu Gln Glu Ser Arg Ala Ile Ala Val Pro Gly
        35                  40                  45

Ser Phe Asn Asp Gln Phe Ala Asp Ala Asp Ile Arg Asn Tyr Ala Gly
    50                  55                  60

Asn Val Trp Tyr Gln Arg Glu Val Phe Ile Pro Lys Gly Trp Ala Gly
65                  70                  75                  80

Gln Arg Ile Val Leu Arg Phe Asp Ala Val Thr His Tyr Gly Lys Val
                85                  90                  95

Trp Val Asn Asn Gln Glu Val Met Glu His Gln Gly Gly Tyr Thr Pro
            100                 105                 110

Phe Glu Ala Asp Val Thr Pro Tyr Val Ile Ala Gly Lys Ser Val Arg
        115                 120                 125
```

-continued

```
Ile Thr Val Cys Val Asn Asn Glu Leu Asn Trp Gln Thr Ile Pro Pro
    130                 135                 140
Gly Met Val Ile Thr Asp Glu Asn Gly Lys Lys Gln Ser Tyr Phe
145                 150                 155                 160
His Asp Phe Phe Asn Tyr Ala Gly Ile His Arg Ser Val Met Leu Tyr
                165                 170                 175
Thr Thr Pro Asn Thr Trp Val Asp Asp Ile Thr Val Val Thr His Val
            180                 185                 190
Ala Gln Asp Cys Asn His Ala Ser Val Asp Trp Gln Val Val Ala Asn
        195                 200                 205
Gly Asp Val Ser Val Glu Leu Arg Asp Ala Asp Gln Gln Val Val Ala
210                 215                 220
Thr Gly Gln Gly Thr Ser Gly Thr Leu Gln Val Val Asn Pro His Leu
225                 230                 235                 240
Trp Gln Pro Gly Glu Gly Tyr Leu Tyr Glu Leu Cys Val Thr Ala Lys
                245                 250                 255
Ser Gln Thr Glu Cys Asp Ile Tyr Pro Leu Arg Val Gly Ile Arg Ser
            260                 265                 270
Val Ala Val Lys Gly Glu Gln Phe Leu Ile Asn His Lys Pro Phe Tyr
        275                 280                 285
Phe Thr Gly Phe Gly Arg His Glu Asp Ala Asp Leu Arg Gly Lys Gly
290                 295                 300
Phe Asp Asn Val Leu Met Val His Asp His Ala Leu Met Asp Trp Ile
305                 310                 315                 320
Gly Ala Asn Ser Tyr Arg Thr Ser His Tyr Pro Tyr Ala Glu Glu Met
                325                 330                 335
Leu Asp Trp Ala Asp Glu His Gly Ile Val Val Ile Asp Glu Thr Ala
            340                 345                 350
Ala Val Gly Phe Asn Leu Ser Leu Gly Ile Gly Phe Glu Ala Gly Asn
        355                 360                 365
Lys Pro Lys Glu Leu Tyr Ser Glu Glu Ala Val Asn Gly Glu Thr Gln
370                 375                 380
Gln Ala His Leu Gln Ala Ile Lys Glu Leu Ile Ala Arg Asp Lys Asn
385                 390                 395                 400
His Pro Ser Val Val Met Trp Ser Ile Ala Asn Glu Pro Asp Thr Arg
                405                 410                 415
Pro Gln Gly Ala Arg Glu Tyr Phe Ala Pro Leu Ala Glu Ala Thr Arg
            420                 425                 430
Lys Leu Asp Pro Thr Arg Pro Ile Thr Cys Val Asn Val Met Phe Cys
        435                 440                 445
Asp Ala His Thr Asp Thr Ile Ser Asp Leu Phe Asp Val Leu Cys Leu
450                 455                 460
Asn Arg Tyr Tyr Gly Trp Tyr Val Gln Ser Gly Asp Leu Glu Thr Ala
465                 470                 475                 480
Glu Lys Val Leu Glu Lys Glu Leu Leu Ala Trp Gln Glu Lys Leu His
                485                 490                 495
Gln Pro Ile Ile Ile Thr Glu Tyr Gly Val Asp Thr Leu Ala Gly Leu
            500                 505                 510
His Ser Met Tyr Thr Asp Met Trp Ser Glu Glu Tyr Gln Cys Ala Trp
        515                 520                 525
Leu Asp Met Tyr His Arg Val Phe Asp Arg Val Ser Ala Val Val Gly
530                 535                 540
```

```
Glu Gln Val Trp Asn Phe Ala Asp Phe Ala Thr Ser Gln Gly Ile Leu
545                 550                 555                 560

Arg Val Gly Gly Asn Lys Lys Gly Ile Phe Thr Arg Asp Arg Lys Pro
            565                 570                 575

Lys Ser Ala Ala Phe Leu Leu Gln Lys Arg Trp Thr Gly Met Asn Phe
        580                 585                 590

Gly Glu Lys Pro Gln Gln Gly Gly Lys Gln Gly Leu Cys Gly Arg Lys
    595                 600                 605

Leu Met Asp Lys Asp Cys Glu Met Lys Arg Thr Thr Leu Asp Ser Pro
610                 615                 620

Leu Gly Lys Leu Glu Leu Ser Gly Cys Glu Gln Gly Leu His Glu Ile
625                 630                 635                 640

Lys Leu Leu Gly Lys Gly Thr Ser Ala Ala Asp Ala Val Glu Val Pro
            645                 650                 655

Ala Pro Ala Ala Val Leu Gly Gly Pro Glu Pro Leu Met Gln Ala Thr
        660                 665                 670

Ala Trp Leu Asn Ala Tyr Phe His Gln Pro Glu Ala Ile Glu Glu Phe
    675                 680                 685

Pro Val Pro Ala Leu His His Pro Val Phe Gln Gln Glu Ser Phe Thr
690                 695                 700

Arg Gln Val Leu Trp Lys Leu Leu Lys Val Val Lys Phe Gly Glu Val
705                 710                 715                 720

Ile Ser Tyr Gln Gln Leu Ala Ala Leu Ala Gly Asn Pro Ala Ala Thr
            725                 730                 735

Ala Ala Val Lys Thr Ala Leu Ser Gly Asn Pro Val Pro Ile Leu Ile
        740                 745                 750

Pro Cys His Arg Val Val Ser Ser Ser Gly Ala Val Gly Gly Tyr Glu
    755                 760                 765

Gly Gly Leu Ala Val Lys Glu Trp Leu Leu Ala His Glu Gly His Arg
770                 775                 780

Leu Gly Lys Pro Gly Leu Gly Pro Ala Gly Ile Gly His His His His
785                 790                 795                 800

His His

<210> SEQ ID NO 5
<211> LENGTH: 885
<212> TYPE: DNA
<213> ORGANISM: Staphylococcus aureus
<220> FEATURE:
<221> NAME/KEY: CDS
<222> LOCATION: (1)..(885)

<400> SEQUENCE: 5 atg gca gat tct gat att aat att aaa acc ggt act aca gat att gga       48
Met Ala Asp Ser Asp Ile Asn Ile Lys Thr Gly Thr Thr Asp Ile Gly
1               5                   10                  15 agc aat act aca gta aaa aca ggt gat tta gtc act tat gat aaa gaa       96
Ser Asn Thr Thr Val Lys Thr Gly Asp Leu Val Thr Tyr Asp Lys Glu
            20                  25                  30 aat ggc atg cac aaa aaa gta ttt tat agt ttt atc gat gat aaa aat      144
Asn Gly Met His Lys Lys Val Phe Tyr Ser Phe Ile Asp Asp Lys Asn
        35                  40                  45 cac aat aaa aaa ctg cta gtt att aga acg aaa ggt acc att gct ggt      192
His Asn Lys Lys Leu Leu Val Ile Arg Thr Lys Gly Thr Ile Ala Gly
    50                  55                  60
```

| | | |
|---|---|---|
| caa tat aga gtt tat agc gaa gaa ggt gct aac aaa agt ggt tta gcc<br>Gln Tyr Arg Val Tyr Ser Glu Glu Gly Ala Asn Lys Ser Gly Leu Ala<br>65                     70                 75                 80 | | 240 |
| tgg cct tca gcc ttt aag gta cag ttg caa cta cct gat aat gaa gta<br>Trp Pro Ser Ala Phe Lys Val Gln Leu Gln Leu Pro Asp Asn Glu Val<br>                 85                 90                 95 | | 288 |
| gct caa ata tct gat tac tat cca aga aat tcg att gat aca aaa gag<br>Ala Gln Ile Ser Asp Tyr Tyr Pro Arg Asn Ser Ile Asp Thr Lys Glu<br>               100                105               110 | | 336 |
| tat atg agt act tta act tat gga ttc aac ggt aat gtt act ggt gat<br>Tyr Met Ser Thr Leu Thr Tyr Gly Phe Asn Gly Asn Val Thr Gly Asp<br>               115                120               125 | | 384 |
| gat aca gga aaa att ggc ggc ctt att ggt gca aat gtt tcg att ggt<br>Asp Thr Gly Lys Ile Gly Gly Leu Ile Gly Ala Asn Val Ser Ile Gly<br>130                     135                140 | | 432 |
| cat aca ctg aaa tat gtt caa cct gat ttc aaa aca att tta gag agc<br>His Thr Leu Lys Tyr Val Gln Pro Asp Phe Lys Thr Ile Leu Glu Ser<br>145                     150                155               160 | | 480 |
| cca act gat aaa aaa gta ggc tgg aaa gtg ata ttt aac aat atg gtg<br>Pro Thr Asp Lys Lys Val Gly Trp Lys Val Ile Phe Asn Asn Met Val<br>               165                170               175 | | 528 |
| aat caa aat tgg gga cca tat gat aga gat tct tgg aac ccg gta tat<br>Asn Gln Asn Trp Gly Pro Tyr Asp Arg Asp Ser Trp Asn Pro Val Tyr<br>               180                185               190 | | 576 |
| ggc aat caa ctt ttc atg aaa act aga aat ggt tct atg aaa gca gca<br>Gly Asn Gln Leu Phe Met Lys Thr Arg Asn Gly Ser Met Lys Ala Ala<br>               195                200               205 | | 624 |
| gat aac ttc ctt gat cct aac aaa gca agt tct cta tta tct tca ggg<br>Asp Asn Phe Leu Asp Pro Asn Lys Ala Ser Ser Leu Leu Ser Ser Gly<br>210                     215                220 | | 672 |
| ttt tca cca gac ttc gct aca gtt att act atg gat aga aaa gca tcc<br>Phe Ser Pro Asp Phe Ala Thr Val Ile Thr Met Asp Arg Lys Ala Ser<br>225                     230                235               240 | | 720 |
| aaa caa caa aca aat ata gat gta ata tac gaa cga gtt cgt gat gat<br>Lys Gln Gln Thr Asn Ile Asp Val Ile Tyr Glu Arg Val Arg Asp Asp<br>               245                250               255 | | 768 |
| tac caa ttg cat tgg act tca aca aat tgg aaa ggt acc aat act aaa<br>Tyr Gln Leu His Trp Thr Ser Thr Asn Trp Lys Gly Thr Asn Thr Lys<br>               260                265               270 | | 816 |
| gat aaa tgg aca gat cgt tct tca gaa aga tat aaa atc gat tgg gaa<br>Asp Lys Trp Thr Asp Arg Ser Ser Glu Arg Tyr Lys Ile Asp Trp Glu<br>275                     280                285 | | 864 |
| aaa gaa gaa atg aca aat taa<br>Lys Glu Glu Met Thr Asn<br>               290 | | 885 |

<210> SEQ ID NO 6
<211> LENGTH: 294
<212> TYPE: PRT
<213> ORGANISM: Staphylococcus aureus

<400> SEQUENCE: 6

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

```
Gln Tyr Arg Val Tyr Ser Glu Glu Gly Ala Asn Lys Ser Gly Leu Ala
 65                  70                  75                  80

Trp Pro Ser Ala Phe Lys Val Gln Leu Gln Leu Pro Asp Asn Glu Val
                 85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn
        290

<210> SEQ ID NO 7
<211> LENGTH: 901
<212> TYPE: PRT
<213> ORGANISM: Artificial Sequence
<220> FEATURE:
<223> OTHER INFORMATION: Halo-tag protein

<400> SEQUENCE: 7

Leu Arg Pro Val Glu Thr Pro Thr Arg Glu Ile Lys Lys Leu Asp Gly
 1               5                  10                  15

Leu Trp Ala Phe Ser Leu Asp Arg Glu Asn Cys Gly Ile Asp Gln Arg
             20                  25                  30

Trp Trp Glu Ser Ala Leu Gln Glu Ser Arg Ala Ile Ala Val Pro Gly
         35                  40                  45

Ser Phe Asn Asp Gln Phe Ala Asp Ala Asp Ile Arg Asn Tyr Ala Gly
     50                  55                  60

Asn Val Trp Tyr Gln Arg Glu Val Phe Ile Pro Lys Gly Trp Ala Gly
 65                  70                  75                  80

Gln Arg Ile Val Leu Arg Phe Asp Ala Val Thr His Tyr Gly Lys Val
                 85                  90                  95

Trp Val Asn Asn Gln Glu Val Met Glu His Gln Gly Gly Tyr Thr Pro
            100                 105                 110

Phe Glu Ala Asp Val Thr Pro Tyr Val Ile Ala Gly Lys Ser Val Arg
        115                 120                 125
```

```
Ile Thr Val Cys Val Asn Asn Glu Leu Asn Trp Gln Thr Ile Pro Pro
130                 135                 140

Gly Met Val Ile Thr Asp Glu Asn Gly Lys Lys Gln Ser Tyr Phe
145                 150                 155                 160

His Asp Phe Phe Asn Tyr Ala Gly Ile His Arg Ser Val Met Leu Tyr
                165                 170                 175

Thr Thr Pro Asn Thr Trp Val Asp Asp Ile Thr Val Val Thr His Val
            180                 185                 190

Ala Gln Asp Cys Asn His Ala Ser Val Asp Trp Gln Val Val Ala Asn
        195                 200                 205

Gly Asp Val Ser Val Glu Leu Arg Asp Ala Asp Gln Gln Val Val Ala
210                 215                 220

Thr Gly Gln Gly Thr Ser Gly Thr Leu Gln Val Val Asn Pro His Leu
225                 230                 235                 240

Trp Gln Pro Gly Glu Gly Tyr Leu Tyr Glu Leu Cys Val Thr Ala Lys
                245                 250                 255

Ser Gln Thr Glu Cys Asp Ile Tyr Pro Leu Arg Val Gly Ile Arg Ser
            260                 265                 270

Val Ala Val Lys Gly Glu Gln Phe Leu Ile Asn His Lys Pro Phe Tyr
        275                 280                 285

Phe Thr Gly Phe Gly Arg His Glu Asp Ala Asp Leu Arg Gly Lys Gly
290                 295                 300

Phe Asp Asn Val Leu Met Val His Asp His Ala Leu Met Asp Trp Ile
305                 310                 315                 320

Gly Ala Asn Ser Tyr Arg Thr Ser His Tyr Pro Tyr Ala Glu Glu Met
                325                 330                 335

Leu Asp Trp Ala Asp Glu His Gly Ile Val Val Ile Asp Glu Thr Ala
            340                 345                 350

Ala Val Gly Phe Asn Leu Ser Leu Gly Ile Gly Phe Glu Ala Gly Asn
        355                 360                 365

Lys Pro Lys Glu Leu Tyr Ser Glu Glu Ala Val Asn Gly Glu Thr Gln
370                 375                 380

Gln Ala His Leu Gln Ala Ile Lys Glu Leu Ile Ala Arg Asp Lys Asn
385                 390                 395                 400

His Pro Ser Val Val Met Trp Ser Ile Ala Asn Glu Pro Asp Thr Arg
                405                 410                 415

Pro Gln Gly Ala Arg Glu Tyr Phe Ala Pro Leu Ala Glu Ala Thr Arg
            420                 425                 430

Lys Leu Asp Pro Thr Arg Pro Ile Thr Cys Val Asn Val Met Phe Cys
        435                 440                 445

Asp Ala His Thr Asp Thr Ile Ser Asp Leu Phe Asp Val Leu Cys Leu
450                 455                 460

Asn Arg Tyr Tyr Gly Trp Tyr Val Gln Ser Gly Asp Leu Glu Thr Ala
465                 470                 475                 480

Glu Lys Val Leu Glu Lys Glu Leu Leu Ala Trp Gln Glu Lys Leu His
                485                 490                 495

Gln Pro Ile Ile Ile Thr Glu Tyr Gly Val Asp Thr Leu Ala Gly Leu
            500                 505                 510

His Ser Met Tyr Thr Asp Met Trp Ser Glu Glu Tyr Gln Cys Ala Trp
        515                 520                 525

Leu Asp Met Tyr His Arg Val Phe Asp Arg Val Ser Ala Val Val Gly
530                 535                 540
```

Glu Gln Val Trp Asn Phe Ala Asp Phe Ala Thr Ser Gln Gly Ile Leu
545                 550                 555                 560

Arg Val Gly Gly Asn Lys Lys Gly Ile Phe Thr Arg Asp Arg Lys Pro
            565                 570                 575

Lys Ser Ala Ala Phe Leu Leu Gln Lys Arg Trp Thr Gly Met Asn Phe
        580                 585                 590

Gly Glu Lys Pro Gln Gln Gly Gly Lys Gln Gly Leu Cys Gly Arg Lys
    595                 600                 605

Leu Met Ala Glu Ile Gly Thr Gly Phe Pro Phe Asp Pro His Tyr Val
610                 615                 620

Glu Val Leu Gly Glu Arg Met His Tyr Val Asp Val Gly Pro Arg Asp
625                 630                 635                 640

Gly Thr Pro Val Leu Phe Leu His Gly Asn Pro Thr Ser Ser Tyr Val
            645                 650                 655

Trp Arg Asn Ile Ile Pro His Val Ala Pro Thr His Arg Cys Ile Ala
        660                 665                 670

Pro Asp Leu Ile Gly Met Gly Lys Ser Asp Lys Pro Asp Leu Gly Tyr
    675                 680                 685

Phe Phe Asp Asp His Val Arg Phe Met Asp Ala Phe Ile Glu Ala Leu
690                 695                 700

Gly Leu Glu Glu Val Val Leu Val Ile His Asp Trp Gly Ser Ala Leu
705                 710                 715                 720

Gly Phe His Trp Ala Lys Arg Asn Pro Glu Arg Val Lys Gly Ile Ala
            725                 730                 735

Phe Met Glu Phe Ile Arg Pro Ile Pro Thr Trp Asp Glu Trp Pro Glu
        740                 745                 750

Phe Ala Arg Glu Thr Phe Gln Ala Phe Arg Thr Thr Asp Val Gly Arg
    755                 760                 765

Lys Leu Ile Ile Asp Gln Asn Val Phe Ile Glu Gly Thr Leu Pro Met
770                 775                 780

Gly Val Val Arg Pro Leu Thr Glu Val Glu Met Asp His Tyr Arg Glu
785                 790                 795                 800

Pro Phe Leu Asn Pro Val Asp Arg Glu Pro Leu Trp Arg Phe Pro Asn
            805                 810                 815

Glu Leu Pro Ile Ala Gly Glu Pro Ala Asn Ile Val Ala Leu Val Glu
        820                 825                 830

Glu Tyr Met Asp Trp Leu His Gln Ser Pro Val Pro Lys Leu Leu Phe
    835                 840                 845

Trp Gly Thr Pro Gly Val Leu Ile Pro Pro Ala Glu Ala Ala Arg Leu
850                 855                 860

Ala Lys Ser Leu Pro Asn Cys Lys Ala Val Asp Ile Gly Pro Gly Leu
865                 870                 875                 880

Asn Leu Leu Gln Glu Asp Asn Pro Asp Leu Ile Gly Ser Glu Ile Ala
            885                 890                 895

Arg Trp Leu Ser Thr
            900

<210> SEQ ID NO 8
<211> LENGTH: 771
<212> TYPE: DNA
<213> ORGANISM: Staphylococcus aureus
<220> FEATURE:
<221> NAME/KEY: CDS
<222> LOCATION: (1)..(771)

```
<400> SEQUENCE: 8 atg ttt tat agt ttt atc gat gat aaa aat cac aat aaa aaa ctg cta      48
Met Phe Tyr Ser Phe Ile Asp Asp Lys Asn His Asn Lys Lys Leu Leu
1               5                  10                  15 gtt att aga acg aaa ggt acc att gct ggt caa tat aga gtt tat agc      96
Val Ile Arg Thr Lys Gly Thr Ile Ala Gly Gln Tyr Arg Val Tyr Ser
            20                  25                  30 gaa gaa ggt gct aac aaa agt ggt tta gcc tgg cct tca gcc ttt aag     144
Glu Glu Gly Ala Asn Lys Ser Gly Leu Ala Trp Pro Ser Ala Phe Lys
        35                  40                  45 gta cag ttg caa cta cct gat aat gaa gta gct caa ata tct gat tac     192
Val Gln Leu Gln Leu Pro Asp Asn Glu Val Ala Gln Ile Ser Asp Tyr
    50                  55                  60 tat cca aga aat tcg att gat aca aaa gag tat atg agt act tta act     240
Tyr Pro Arg Asn Ser Ile Asp Thr Lys Glu Tyr Met Ser Thr Leu Thr
65                  70                  75                  80 tat gga ttc aac ggt aat gtt act ggt gat gat aca gga aaa att ggc     288
Tyr Gly Phe Asn Gly Asn Val Thr Gly Asp Asp Thr Gly Lys Ile Gly
                85                  90                  95 ggc ctt att ggt gca aat gtt tcg att ggt cat aca ctg aaa tat gtt     336
Gly Leu Ile Gly Ala Asn Val Ser Ile Gly His Thr Leu Lys Tyr Val
            100                 105                 110 caa cct gat ttc aaa aca att tta gag agc cca act gat aaa aaa gta     384
Gln Pro Asp Phe Lys Thr Ile Leu Glu Ser Pro Thr Asp Lys Lys Val
        115                 120                 125 ggc tgg aaa gtg ata ttt aac aat atg gtg aat caa aat tgg gga cca     432
Gly Trp Lys Val Ile Phe Asn Asn Met Val Asn Gln Asn Trp Gly Pro
    130                 135                 140 tat gat aga gat tct tgg aac ccg gta tat ggc aat caa ctt ttc atg     480
Tyr Asp Arg Asp Ser Trp Asn Pro Val Tyr Gly Asn Gln Leu Phe Met
145                 150                 155                 160 aaa act aga aat ggt tct atg aaa gca gca gat aac ttc ctt gat cct     528
Lys Thr Arg Asn Gly Ser Met Lys Ala Ala Asp Asn Phe Leu Asp Pro
                165                 170                 175 aac aaa gca agt tct cta tta tct tca ggg ttt tca cca gac ttc gct     576
Asn Lys Ala Ser Ser Leu Leu Ser Ser Gly Phe Ser Pro Asp Phe Ala
            180                 185                 190 aca gtt att act atg gat aga aaa gca tcc aaa caa caa aca aat ata     624
Thr Val Ile Thr Met Asp Arg Lys Ala Ser Lys Gln Gln Thr Asn Ile
        195                 200                 205 gat gta ata tac gaa cga gtt cgt gat gat tac caa ttg cat tgg act     672
Asp Val Ile Tyr Glu Arg Val Arg Asp Asp Tyr Gln Leu His Trp Thr
    210                 215                 220 tca aca aat tgg aaa ggt acc aat act aaa gat aaa tgg aca gat cgt     720
Ser Thr Asn Trp Lys Gly Thr Asn Thr Lys Asp Lys Trp Thr Asp Arg
225                 230                 235                 240 tct tca gaa aga tat aaa atc gat tgg gaa aaa gaa gaa atg aca aat     768
Ser Ser Glu Arg Tyr Lys Ile Asp Trp Glu Lys Glu Glu Met Thr Asn
                245                 250                 255 taa                                                                  771

<210> SEQ ID NO 9
<211> LENGTH: 256
<212> TYPE: PRT
<213> ORGANISM: Staphylococcus aureus
```

```
<400> SEQUENCE: 9

Met Phe Tyr Ser Phe Ile Asp Asp Lys Asn His Asn Lys Lys Leu Leu
1               5                   10                  15

Val Ile Arg Thr Lys Gly Thr Ile Ala Gly Gln Tyr Arg Val Tyr Ser
                20                  25                  30

Glu Glu Gly Ala Asn Lys Ser Gly Leu Ala Trp Pro Ser Ala Phe Lys
            35                  40                  45

Val Gln Leu Gln Leu Pro Asp Asn Glu Val Ala Gln Ile Ser Asp Tyr
    50                  55                  60

Tyr Pro Arg Asn Ser Ile Asp Thr Lys Glu Tyr Met Ser Thr Leu Thr
65                  70                  75                  80

Tyr Gly Phe Asn Gly Asn Val Thr Gly Asp Asp Thr Gly Lys Ile Gly
                85                  90                  95

Gly Leu Ile Gly Ala Asn Val Ser Ile Gly His Thr Leu Lys Tyr Val
            100                 105                 110

Gln Pro Asp Phe Lys Thr Ile Leu Glu Ser Pro Thr Asp Lys Lys Val
            115                 120                 125

Gly Trp Lys Val Ile Phe Asn Asn Met Val Asn Gln Asn Trp Gly Pro
130                 135                 140

Tyr Asp Arg Asp Ser Trp Asn Pro Val Tyr Gly Asn Gln Leu Phe Met
145                 150                 155                 160

Lys Thr Arg Asn Gly Ser Met Lys Ala Ala Asp Asn Phe Leu Asp Pro
                165                 170                 175

Asn Lys Ala Ser Ser Leu Leu Ser Ser Gly Phe Ser Pro Asp Phe Ala
            180                 185                 190

Thr Val Ile Thr Met Asp Arg Lys Ala Ser Lys Gln Gln Thr Asn Ile
        195                 200                 205

Asp Val Ile Tyr Glu Arg Val Arg Asp Asp Tyr Gln Leu His Trp Thr
        210                 215                 220

Ser Thr Asn Trp Lys Gly Thr Asn Thr Lys Asp Lys Trp Thr Asp Arg
225                 230                 235                 240

Ser Ser Glu Arg Tyr Lys Ile Asp Trp Glu Lys Glu Glu Met Thr Asn
                245                 250                 255
```

IN VITRO MEMBRANE PROTEIN MOLECULAR EVOLUTIONARY ENGINEERING TECHNIQUE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 390051_407USPC_SEQUENCE_LISTING.txt. The text file is 42.6 KB, was created on Dec. 29, 2014, and is being submitted electronically via EFS-Web.

TECHNICAL FIELD

The present invention relates to the field of novel unilamellar liposomes for utilization in in-vitro molecular evolutionary engineering of membrane proteins. The present invention further relates to novel molecular evolutionary engineering, particularly enzyme evolutionary engineering, targeting membrane proteins that uses the unilamellar liposomes.

BACKGROUND ART

As a method of improving an enzyme by evolutionary engineering, a method using liposomes in which a gene library and a cell-free protein synthesis system are enclosed, and a cell sorter has been utilized. In this method, a gene library in which random mutation is introduced into an enzyme gene and a cell-free protein synthesis system are enclosed in liposomes for internal expression of an enzyme. Further, a liposome that contains an enzyme having a higher function is selected by the cell sorter to enable selection of a gene encoding an enzyme having a higher function. By repeating this selection, a gene encoding an enzyme can be evolved (Non Patent Literature 1). This conventional method is solely targeted to soluble proteins.

It is well known that membrane proteins play an important role in functions of cells. Thus, novel molecular evolutionary engineering, particularly enzyme evolutionary engineering, targeting membrane proteins has been required.

CITATION LIST

Non Patent Literature

[NPL 1] Sunami, T., Sato, K., Matsuura, T., Tsukada, K., Urabe, I., and Yomo, T. (2006) Analytical biochemistry 357, 128-136

SUMMARY OF INVENTION

Technical Problem

The objective of the present invention is to provide a novel molecular evolutionary engineering technique, particularly an enzyme evolutionary engineering technique, targeting membrane proteins.

Solution to Problem

The above-described objective has been achieved by providing the following.

(Item 1)
A unilamellar liposome comprising:
(a) a DNA comprising a promoter sequence, a translational initiation sequence, and a sequence encoding a membrane protein;
(b) an RNA polymerase;
(c) a ribonucleotide; and
(d) a cell-free protein synthesis system.

(Item 2)
The unilamellar liposome of item 1, wherein the membrane protein is a transporter, and the unilamellar liposome further comprises
(e) a factor that binds to a ligand transported by the membrane protein.

(Item 3)
The unilamellar liposome of item 1 or 2, wherein the unilamellar liposome is treated with a nuclease.

(Item 4)
The unilamellar liposome of item 3, wherein the nuclease is selected from the group consisting of a ribonuclease and a deoxyribonuclease.

(Item 5)
The unilamellar liposome of item 4, wherein the nuclease is a ribonuclease.

(Item 6)
A library comprising a plurality of unilamellar liposomes, wherein the unilamellar liposome comprises:
(a) a DNA comprising a promoter sequence, a translational initiation sequence, and a sequence encoding a membrane protein;
(b) an RNA polymerase;
(c) a ribonucleotide; and
(d) a cell-free protein synthesis system.

(Item 7)
The library of item 6, wherein the membrane protein is a transporter, and the unilamellar liposome further comprises
(e) a factor that binds to a ligand transported by the membrane protein.

(Item 8)
The library of item 6 or 7, wherein the unilamellar liposome is treated with a nuclease.

(Item 9)
The library of item 8, wherein the nuclease is selected from the group consisting of a ribonuclease and a deoxyribonuclease.

(Item 10)
The library of item 9, wherein the nuclease is a ribonuclease.

(Item 11)
A unilamellar liposome comprising:
(a) an RNA comprising a translational initiation sequence, and a sequence encoding a membrane protein; and
(d) a cell-free protein synthesis system.

(Item 12)
The unilamellar liposome of item 11, wherein the membrane protein is a transporter, and the unilamellar liposome further comprises
(e) a factor that binds to a ligand transported by the membrane protein.

(Item 13)
The unilamellar liposome of item 11 or 12, wherein the unilamellar liposome is treated with a nuclease.

(Item 14)
The unilamellar liposome of item 13, wherein the nuclease is selected from the group consisting of a ribonuclease and a deoxyribonuclease.

(Item 15)
The unilamellar liposome of item 14, wherein the nuclease is a ribonuclease.
(Item 16)
A library comprising a plurality of unilamellar liposomes, wherein the unilamellar liposome comprises:
(a) an RNA comprising a translational initiation sequence, and a sequence encoding a membrane protein; and
(d) a cell-free protein synthesis system.
(Item 17)
The library of item 16, wherein the membrane protein is a transporter, and the unilamellar liposome further comprises
(e) a factor that binds to a ligand transported by the membrane protein.
(Item 18)
The library of item 16 or 17, wherein the unilamellar liposome is treated with a nuclease.
(Item 19)
The library of item 18, wherein the nuclease is selected from the group consisting of a ribonuclease and a deoxyribonuclease.
(Item 20)
The library of item 19, wherein the nuclease is a ribonuclease.
(Item 21)
A method of producing a unilamellar liposome treated with a nuclease, comprising:
(1) preparing a unilamellar liposome enclosing:
(a) a DNA comprising a promoter sequence, a translational initiation sequence, and a sequence encoding a membrane protein;
(b) an RNA polymerase;
(c) a ribonucleotide; and
(d) a cell-free protein synthesis system; and
(2) treating the unilamellar liposome prepared in (1) with a nuclease.
(Item 22)
A method of producing a unilamellar liposome treated with a nuclease, comprising:
(1) preparing a unilamellar liposome enclosing:
(a) a DNA comprising a promoter sequence, a translational initiation sequence, and a sequence encoding a membrane protein that is a transporter;
(b) an RNA polymerase;
(c) a ribonucleotide;
(d) a cell-free protein synthesis system; and
(e) a factor that binds to a ligand transported by the membrane protein; and
(2) treating the unilamellar liposome prepared in (1) with a nuclease.
(Item 23)
The method of item 21 or 22, wherein the nuclease is selected from the group consisting of a ribonuclease and a deoxyribonuclease.
(Item 24)
The method of item 23, wherein the nuclease is a ribonuclease.
(Item 25)
A method of producing a unilamellar liposome treated with a nuclease, comprising:
(1) preparing a unilamellar liposome enclosing:
(a) an RNA comprising a translational initiation sequence, and a sequence encoding a membrane protein; and
(d) a cell-free protein synthesis system; and
(2) treating the unilamellar liposome prepared in (1) with a nuclease.
(Item 26)
A method of producing a unilamellar liposome treated with a nuclease, comprising:
(1) preparing a unilamellar liposome enclosing:
(a) an RNA comprising a translational initiation sequence, and a sequence encoding a membrane protein that is a transporter;
(d) a cell-free protein synthesis system; and
(e) a factor that binds to a ligand transported by the membrane protein; and
(2) treating the unilamellar liposome prepared in (1) with a nuclease.
(Item 27)
The method of item 25 or 26, wherein the nuclease is selected from the group consisting of a ribonuclease and a deoxyribonuclease.
(Item 28)
The method of item 27, wherein the nuclease is a ribonuclease.
(Item 29)
A screening method using a library of unilamellar liposomes, comprising:
(i) providing a library of any of items 6 to 10;
(ii) selecting a unilamellar liposome having a desired feature from the library;
(iii) amplifying a DNA included in the unilamellar liposome; and
(iv) isolating the amplified DNA.
(Item 30)
A screening method using a library of unilamellar liposomes, comprising:
(i) providing a library of any of items 16 to 20;
(ii) selecting a unilamellar liposome having a desired feature from the library;
(iii) generating a DNA by operating a reverse transcriptase on an RNA included in the unilamellar liposome;
(iv) amplifying the generated DNA; and
(v) isolating the amplified DNA.

Advantageous Effects of Invention

The present invention enables an in-vitro molecular evolutionary engineering technique targeting membrane proteins that utilizes liposomes. The present invention further enables large-scale screening/selection of a gene encoding a membrane protein having a desired function.

If a membrane protein is a transporter, a factor that binds to a ligand transported by the membrane protein would be enclosed within a liposome to capture the transported ligand within the liposome, thereby enhancing the sensitivity of screening/selection.

Further, by using unilamellar liposomes that are processed by a nuclease according to the present invention, screening efficiency will be enhanced. While not wishing to be bound by theory, the following reason can be mentioned as a reason that the present invention exerts a remarkable effect. Conventionally-used liposomes are multilamellar liposomes that are prepared by a freeze-drying method, and since those liposomes internally have a multiple structure, the volume of a reaction vessel is not possible to be controlled. The volume of liposomes affects the internal enzymatic kinetics. Thus, in order to efficiently improve an enzyme, the use of unilamellar liposomes which do not have a multiple structure is preferable. However, in methods so far, when unilamellar liposomes that are prepared by a centrifugal sedimentation method are used as reaction vessels, selection and collection of a gene encoding an enzyme having a high function were not possible even by selecting liposomes that were more reactive than others by a cell sorter. In contrast, in the present invention, treatment of unilamellar liposomes with a nuclease enables further highly-efficient screening compared to unilamellar liposomes that are not treated with an enzyme and multilamellar liposomes used in conventional methods, thereby allowing selection and collection of a gene encoding a highly-functional enzyme.

In addition, by optimizing the composition/ratio of a lipid forming a liposome and the magnesium concentration when preparing the liposome according to the disclosure of the present invention, the sensitivity of screening/selection will be further enhanced.

BRIEF DESCRIPTION OF DRAWINGS

FIG. 1 is the result of using a DNA comprising an EmrE-myc-his sequence (SEQ ID NO: 1) or a DNA comprising a GUS sequence (SEQ ID NO: 3), wherein a labeling anti-Myc tag antibody is added to liposomes before and after the expression of proteins, and an analysis is performed by a cell sorter. The vertical axis shows the internal volume of liposomes and the horizontal axis shows the fluorescence intensity of Alexa 488. A and B show the results of using the GUS sequence, and C and D show the results of using the EmrE-myc-his sequence. A and C are results of liposomes before the expression of proteins by incubation at 37° C., and B and D are results of liposomes that expressed proteins by an hour incubation at 37° C.

FIG. 2 is the result of measuring the transport activity of EtBr with different pH, in liposomes comprising a DNA comprising an EmrE-myc-his sequence (SEQ ID NO: 1; FIG. 2A) or a DNA comprising a GUS sequence (SEQ ID NO: 3; FIG. 2B), wherein proteins are expressed.

FIG. 3 is the result showing the percentage of expression of a membrane protein having a function when various lipid compositions are used. When hemolysin exerts the activity, Halo Tag Alexa Fluor 488 ligand is taken in with high intensity, and thus the vertical axis shows the percentage (%) of liposomes that taken in ligands with high intensity. That is, the vertical axis shows the percentage of exertion of membrane protein activity in liposomes. The results of using the mixture of POPC:Chol=9:1; the mixture of POPC: Chol=7:3; the mixture of POPC:Chol=5:5; and the mixture of POPC:Chol=3:7 are shown in order from the left. Further, POPC is an abbreviation of 1-palmitoyl-2-oleoylphosphatidylcholine, and Chol is an abbreviation of cholesterol.

FIG. 4 The vertical axis of FIG. 4 shows the percentage (%) of liposomes that taken in Halo Tag Alexa Fluor 488 ligand with high intensity among all the liposomes when various lipids are used. That is, FIG. 4 is a graph showing the relative activity of channels. The lipids that are used are as follows: EggPC is an abbreviation of phosphatidylcholine purified from a hen's egg; POPC is an abbreviation of 1-palmitoyl-2-oleoylphosphatidylcholine; PS is an abbreviation of 1-palmitoyl-2-oleoylphosphoserine; PE is an abbreviation of 1-palmitoyl-2-oleoylphosphoethanolamine; and Chol is an abbreviation of cholesterol. PC mix is an abbreviation of the mixture of 1-palmitoyl-2-oleoylphosphatidylcholine:1-palmitoyl-2-linoleoylphosphatidylcholine:1-stearoyl-2-oleoylphosphatidylcholine:1-stearoyl-2-linoleoylphosphatidylcholine=129:67:48:24 (mass ratio); EggPC/PS/PE is an abbreviation of the mixture of each of them at the ratio of 3:1:1 (mass ratio) in order; EggPC/PS/PE/Chol is an abbreviation of the mixture of each of them at the ratio of 2:1:1:1 (mass ratio) in order; PCmix/PS/PE is an abbreviation of the mixture of each of them at the ratio of 3:1:1 (mass ratio) in order; PCmix/PS/PE/Chol is an abbreviation of the mixture of each of them at the ratio of 2:1:1:1 (mass ratio) in order; POPC/PS/PE is an abbreviation of the mixture of each of them at the ratio of 3:1:1 (mass ratio) in order; and POPC/POPE/POPS/Chol is an abbreviation of the mixture of each of them at the ratio of 2:1:1:1 (mass ratio) in order.

FIG. 5 is a graph showing the result of an evolutionary experiment. The vertical axis shows the percentage of high intensity liposomes (the percentage of red dots). By repeating the cycle, the percentage of a group having high activity increased.

DESCRIPTION OF EMBODIMENTS

Hereinafter, the present invention will be described. It should be understood that unless particularly stated otherwise, the terms used in the present specification have the meanings that are conventionally used in the art.

Hereinafter, the definitions of the terms that are used particularly in the present specification will be listed.
(Definition)

The term "micro-compartment" as used herein refers to a closed minute space composed of a lipid layer and an internal aqueous layer. Examples of the "micro-compartment" include liposomes, but are not limited thereto.

The term "liposome" as used herein generally means a closed vesicle composed of a lipid layer gathered in a membrane state and an internal aqueous layer. Other than phospholipid which is representatively used, cholesterol, glycolipid and the like can be incorporated. In the present invention, a liposome preferably contains cholesterol as the component. In the present invention, in order to have a modifying group, a liposome may have a constitutional unit having a functional group that allows ester bond (for example, glycolipid, ganglioside and phosphatidylglycerol) or a constitutional unit having a functional group that allows peptide bond (for example, phosphatidylethanolamine). The liposome that is used in the present invention is a "unilamellar liposome" consisting of a single membrane consisting of a lipid bilayer. As the preparation method of the unilamellar liposome, various well-known methods can be utilized.

The term "promoter sequence" as used herein refers to a region on a DNA that determines an initiation site of transcription of a gene and that directly regulates the frequency thereof, which is a base sequence to which an RNA polymerase bound and starts transcription. Although a putative promoter region varies in each structural gene, a putative promoter region is generally located in the upstream of a structural gene. However, the location is not limited thereto, and a putative promoter region also may be located in the downstream of a structural gene. The promoter may be inducible, structural, site-specific or stage-specific. The promoter may be any promoter as long as the promoter is able to be expressed in a host cell such as a mammalian cell, a colon *bacillus* and yeast. Representative promoter sequences include a T7 promoter sequence, a T5 promoter sequence, a Sp6 promoter sequence and a T3 promoter sequence, but are not limited thereto.

The "RNA polymerase" as used herein may be any RNA polymerase as long as it adapts to a promoter sequence to be used, that is, performs transcription from the promoter to be used. Preferably, the promoter sequence and the RNA polymerase are derived from the same or close species. For example, when a promoter sequence derived from a prokaryote is used, an RNA polymerase to be used is also preferably derived from a prokaryote. Alternatively, when a promoter sequence derived from a bacteriophage is used, an RNA polymerase to be used is also preferably derived from the same or similar bacteriophage.

The term "translational initiation sequence" as used herein means any sequence that is able to provide a functional ribosome entry site. In the system of bacteria, this region is also referred to as Shine-Dalgarno sequence.

The term "cell-free protein synthesis system" as used herein is a component derived from a cell that has lost autonomous replication ability by treating the cell, and is a component that is able to synthesize a protein. As the cell-free protein synthesis system, for example, PURESYS-TEM (registered trademark) (BioComber Co., Ltd.; Bun-kyo-ku, Tokyo) that is commercially available can be utilized. Alternatively, the cell-free protein synthesis system is possible to be prepared by performing purification and/or recombinant expression of a component that is required for the cell-free protein synthesis system.

The term "operably linked" as used herein refers to a state in which the expression (operation) of a desired sequence is disposed under the control of a certain transcriptional/translational regulatory sequence (for example, a promoter and an enhancer) or a translational regulatory sequence. In order to allow for a promoter to be operably linked to a gene, the promoter is generally disposed in just upstream of the gene. However, the promoter is not necessarily adjacently disposed.

The term "membrane protein" as used herein refers to a protein that is attached to a lipid bilayer. The membrane protein may be a protein that contains a transmembrane region or may be a protein that does not contain a transmembrane region.

(Membrane Protein)

The present invention is applicable to various membrane proteins. Representative membrane proteins include, for example, transporters and receptors, but are not limited thereto. The sequence encoding the membrane protein of the present invention may comprise a leader sequence for inserting a protein into a membrane, as necessary.

(Transporter)

The membrane protein of the present invention may be or may not be a transporter. Examples of the transporter of the present invention include proteins related to substance transportation in cells (for example, EmrE protein) and proteins that allow permeation of a substance that does not permeate a lipid bilayer (for example, hemolysin), but are not limited thereto.

(Production of Unilamellar Liposome)

The unilamellar liposome used in the present invention is possible to be prepared by using the centrifugal sedimentation method described in the Examples. However, the preparation method is not limited thereto. For example, other than the centrifugal sedimentation method, a swelling hydration method (P. Mueller and T. F. Chien, Biophys. J., 1983, 44, 375-381) and an electro-formation method (Miglena I. Angelove and Dimiter S. Dimitrov, Faraday Discuss. Chem. Soc., 1986, 81, 303-311) can be utilized.

The swelling hydration method is a method that representatively encompasses the following steps: (1) a step of dissolving a lipid in a solvent for natural drying within a flask to form a lipid membrane on a surface of the flask; and (2) a step of adding an aqueous solution to enlarge the lipid membrane. By this second step, a liposome in which the lipid membrane taken in the aqueous solution floats up.

The electro-formation method is a method that representatively encompasses the following steps: (1) a step of applying a lipid solution on a conductive electrode for drying to form a lipid film; (2) a step of placing a conductive electrode also in the opposite side intervened by an insulating spacer and filling an aqueous solution therebetween; and (3) a step of applying an electric field between the two electrodes to remove the lipid film from the electrodes and prepare a giant thin film liposome.

(Component/Composition of Lipid Used in Production of Unilamellar Liposome)

The component/composition of a lipid used in the production of unilamellar liposomes preferably include, although not particularly limited, phospholipid and cholesterol. Examples of the lipid include L-alpha-phosphatidyl-choline, cholesterol, L-alpha-dilauroylphosphatidylcholine, L-alpha-dilauroylphosphatidylethanolamine, L-alpha-dilauroylphosphatidylglycerolsodium, L-alpha-monomyristoyl-phosphatidylcholine, L-alpha-dimyristoylphosphatidylcholine, L-alpha-dimyristoylphosphatidylethanolamine, L-alpha-dimyristoylphosphatidylglycerol ammonium, L-alpha-dimyristoylphosphatidylglycerol sodium, L-alpha-dimyristoylphosphatidic acid sodium, L-alpha-dioleylphosphatidylcholine, L-alpha-dioleoylphosphatidylethanolamine, L-alpha-dioleoylphosphatidylserine sodium, L-alpha-monopalmitoylphosphatidylcholine, L-alpha-dipalmitoylphosphatidylcholine, L-alpha-dipalmitoylphosphatidylethanolamine, L-alpha-dipalmitoylphosphatidylglycerol ammonium, L-alpha-dipalmitoylphosphatidylglycerol sodium, L-alpha-dipalmitoylphosphatidic acid sodium, L-alpha-stearoylphosphatidylcholine, L-alpha-distearoylphosphatidylcholine, L-alpha-distearoylphosphatidylethanolamine, L-alpha-distearoylphosphatidylglycerol sodium, L-alpha-distearoylphosphatidylglycerol ammonium, L-alpha-distearoylphosphatidic acid sodium, L-alpha-dierucoylphosphatidylcholine, 1-palmitoyl-2-oleoylphosphatidylcholine, beta-oleyl-gamma-palmitoyl-L-alpha-phosphatidylethanolamine, beta-oleyl-gamma-palmitoyl-L-alpha-phosphatidylglycerol sodium, sphingomyelin and stearylamine, but are not limited thereto.

The proportion of the cholesterol is preferably 10% or more, more preferably 30% or more, even more preferably 50% or more, and most preferably 700 or more.

(Magnesium Concentration Appropriate for Production of Unilamellar Liposome)

The concentration of magnesium is preferably 15 mM to 50 mM, more preferably 18.88 mM to 42.48 mM, even more preferably 28.32 mM to 37.76 mM, and most preferably 33.04 mM.

(Nuclease)

Examples of the nuclease used in the present invention include a ribonuclease and a deoxyribonuclease, but are not limited thereto. The source of supply of the nuclease to be used is not particularly limited. When DNase is used as the nuclease, the enzyme activity to be used is 1 U to 20 U, more preferably 5 U to 15 U and most preferably about 12.5 U per 100 μL of a liposome solution. When RNase is used as the nuclease, enzyme activity to be used is 1 μg to 20 μg, more preferably 5 μg to 15 μg, and most preferably about 10 μg per 100 μL of a liposome solution. Those skilled in the art are able to readily determine the amount of an enzyme to be used.

(DNA or RNA to be Used)

For example, if genetic information to be included in a liposome is a DNA, a coding sequence of a protein, a translational regulatory sequence operably linked to the coding sequence, and a transcriptional/translational regulatory sequence operably linked to the coding sequence will be included in the DNA.

Examples of the translational regulatory sequence include a translational initiation sequence, but are not limited thereto. A translation termination codon may be included as necessary. The translational regulatory sequence to be linked preferably adapts to a cell-free protein synthesis system to be used. For example, if a cell-free protein synthesis system that is derived from *E. coli* is to be utilized, a translational regulatory sequence to be linked is preferably a translational initiation sequence of *E. coli*. A translational regulatory sequence and a cell-free protein synthesis system to be used are not necessarily required to be derived from the same species. A translational regulatory sequence and a cell-free protein synthesis system to be used can be derived from any species as long as they are adaptable, that is, the cell-free protein synthesis system is able to initiate translation from the translational regulatory sequence.

Examples of the transcriptional/translational regulatory sequence include a promoter sequence, but are not limited thereto. An enhancer sequence, a suppressor sequence, an operator sequence, and a transcription termination site may be included as necessary. A transcriptional/translational regulatory sequence to be linked preferably adapts to an RNA polymerase to be used. For example, if an RNA polymerase derived from *E. coli* is to be utilized, a transcriptional/translational regulatory sequence to be linked is preferably a transcriptional/translational regulatory sequence of *E. coli*. A transcriptional/translational regulatory sequence and an RNA polymerase to be used are not necessarily required to be derived from the same species. The transcriptional/translational regulatory sequence and the RNA polymerase to be used can be derived from any species as long as they are adaptable, that is, the RNA polymerase is able to initiate (or control) transcription from the transcriptional/translational regulatory sequence.

For example, if genetic information to be included in a liposome is an RNA, a coding sequence of a protein, and a translational regulatory sequence operably linked to the coding sequence will be included in the RNA. Examples of the translational regulatory sequence include a translational initiation sequence, but are not limited thereto. A translation termination codon may be included as necessary. A translational regulatory sequence to be linked preferably adapts to a cell-free protein synthesis system to be used. For example, if a cell-free protein synthesis system derived from *E. coli* is to be utilized, a translational regulatory sequence to be linked is preferably a translational initiation sequence of *E. coli*. A translational regulatory sequence and a cell-free protein synthesis system to be used are not necessarily required to be derived from the same species. A translational regulatory sequence and a cell-free protein synthesis system to be used can be derived from any species as long as they are adaptable, that is, the cell-free protein synthesis system is able to initiate translation from the translational regulatory sequence.

(Application of Liposome of the Present Invention to Molecular Evolutionary Engineering)

The liposomes of the present invention can be utilized for molecular evolutionary engineering.

For example, unilamellar liposomes treated by a nuclease are incubated under the condition that the internal DNA or RNA generates protein products, and (1) by using the presence of proteins expressed on the surface of the liposomes as an indicator, or (2) by measuring the activity of the generated membrane proteins and using this activity as an indicator, selection (screening) of unilamellar liposomes including high-functional genetic information is performed. Activity to be utilized is representatively activity of a protein that is encoded by a DNA or an RNA within the unilamellar liposomes. For example, if a DNA or an RNA within the unilamellar liposomes encodes a transporter, activity to be utilized is representatively the transport activity thereof. If the transport activity of a transporter is used as an indicator, for example, substances that are transported into the liposomes by the transporter are labeled (for example, fluorescent labeling), and liposomes in which the labeled substances are accumulated are selected by using a cell sorter (FACS: fluorescence-activated cell sorter). For example, a factor that binds to a ligand transported by the transporter can be enclosed within the liposomes to capture the transported ligand within the liposomes, thereby enhancing the sensitivity of screening/selection.

Alternatively, the enzyme activity possessed by a membrane protein may be used as an indicator.

In order to detect phosphorylation of a protein or bonding with other proteins as an indicator of the activity of a membrane protein, for example, the following methods are used: a step of labeling an edge of a target protein with fluorescent dye that causes FRET; and when conformation is changed by phosphorylation or bonding with other proteins and the degree of FRET is changed, a step of selection by using the fluorescence change as an indicator. Alternatively, by disposing a GFP gene in the downstream of a T3RNA polymerase promoter for example, and using a T3RNA polymerase RNA at the same time, a T3RNA polymerase having higher RNA synthetic activity is possible to be obtained.

In addition, by introducing mutation into sequences (sequences related to the control of gene expression such as a promoter sequence, an enhancer sequence, a ribosome-binding sequence, and a translation initiation site) other than a coding sequence of a protein, and selecting the sequence to which mutation is introduced, a sequence can be evolved to have high activity (for example, high promoter activity, enhancer activity and translation activity).

The unilamellar liposome obtained as a result of screening is used to isolate genetic information included therein as a DNA or an RNA. If the genetic information is a DNA, the isolation can be performed by using a primer that specifically amplifies the DNA, thereby amplifying the genetic information by PCR. Alternatively, if the DNA includes a sequence that is required for autonomous replication within a host cell, the DNA can be introduced into an appropriate host cell, and the isolation can be performed after the amplification.

If genetic information is an RNA, (1) the RNA may be converted into a DNA using a reverse transcriptase, and then the DNA may be amplified by PCR using a thermostable DNA polymerase enzyme, or (2) genetic information of the RNA may be amplified in a single step using a thermostable reverse transcriptase. If the RNA includes a sequence that is required for autonomous replication within a host cell, the RNA can be introduced into an appropriate host cell, and the isolation can be performed after the amplification.

Genetic information is not necessarily required to be isolated (purified) after a first round of screening. For example, instead of obtaining a monoclonal DNA or RNA by the first round of screening, a second round of screening may be performed by obtaining a group of DNAs or RNAs and using the group as a starting material. A group of DNAs or RNAs obtained by the second round of screening or the subsequent rounds of screening may be used as a starting material of the next round.

Alternatively, mutagenesis may be performed on a clone (purified clone) obtained after the screening to prepare a group comprising a plurality of different clones, and the group may be used as a starting material of the screening of the next round.

EXAMPLES

Hereinafter, the present invention will be described in detail by Examples and the like. However, the present invention is not limited thereto.

Example 1: Preparation of Unilamellar Liposome

Unilamellar liposomes were prepared by the centrifugal sedimentation method described below.

10 mg of lipid (phosphatidylcholine:cholesterol=9:1) was dissolved into 100 µl of chloroform for mixture with 2 ml of liquid paraffin.

Incubation was performed for 30 minutes at 80° C.

An extraliposomal solution (333 mM glucose, and a solution in which a group of translated proteins and tRNA are removed from a cell-free protein synthesis system) and an intraliposomal solution (330 mM sucrose, 1 µM Transferrin Alexa 647, a cell-free protein synthesis system, 40 U/µl RNase inhibitor (Promega), 0.4 µM ribosome S1 subunit and 50 pM DNA) were prepared. A DNA comprising an EmrE-myc-his sequence (SEQ ID NO: 1; a sequence comprising a myc tag and a his tag in the C-terminus of an EmrE gene) or a DNA comprising a GUS sequence (SEQ ID NO: 3; negative control comprising a myc sequence and a GUS sequence) was used. This condition is a condition that a single molecule of DNA is enclosed in each liposome. The composition of the cell-free protein synthesis system that was used is as follows: amino acids 0.3 mM each (alanine, glycine, leucine, isoleucine, valine, serine, threonine, proline, tryptophan, phenylalanine, glutamine, glutamic acid, asparagine, aspartic acid, lysine, arginine, histidine, methionine, cysteine, tyrosine); 3.6 µg/µl tRNA; 2 mM ATP; 2 mM GTP; 1 mM CTP; 1 mM UTP; 14 mM magnesium acetate; 50 mM Hepes-KOH (pH7.8); 100 mM potassium glutamate; 2 mM spermidine; 20 mM creatine phosphate; 2 mM dithiothreitol; 10 ng/µl 10-formyl-5.6.7.8.-tetrahydrofolic acid; a group of translated proteins (2500 nM IF1, 411 nM IF2, 728 nM IF3, 247 nM RF1, 484 nM RF2, 168 nM RF3, 485 nM RRF, 727 nM AlaRS, 99 nM ArgRS, 420 nM AsnRS, 121 nM AspRS, 100 nM CysRS, 101 nM GlnRS, 232 nM GluRS, 86 nM GlyRS, 85 nM HisRS, 365 nM IleRS, 99 nM LeuRS, 115 nM LysRS, 109 nM MetRS, 134 nM PheRS, 166 nM ProRS, 99 nM SerRS, 84 nM ThrRS, 102 nM TrpRS, 101 nM TyrRS, 100 nM ValRS, 588 nM MTF, 926 nM MK, 465 nM CK, 1307 nM NDK, 621 nM Ppiase2, 1290 nM EF-G, 2315 nM EF-Tu, 3300 nM EF-Ts, 529 nM Tig, 22 nM HrpA, 1440 nM TrxC).

20 µl of intraliposomal solution was put into 400 µl of liquid paraffin in which a lipid is dissolved, and the solution was placed on ice for 1 minute.

Emulsion was prepared by stirring for 40 seconds at the maximum strength of a vortex mixer, and the emulsion was placed on ice for 10 minutes.

150 µl of extraliposomal solution was put into a new tube and the prepared emulsion was laminated thereon, and they were placed on ice for 10 minutes.

Centrifugation was performed for 30 minutes at 14 k×g, 4° C.

A hole was made at the bottom of the tube, and 80 µl of liposome suspension accumulated at the bottom was collected.

2 µl of 5 U/µl DNase or 4 mg/ml RNase was added to the liposome suspension.

The liposome suspension was incubated for 3 hours at 37° C., and protein synthesis was performed.

An antibody (anti-Myc tag antibody (mouse IgG1) labeled with Alexa Fluor 488) was diluted with a PBS+1% BSA solution and added to the liposome suspension such that the final concentration becomes 5 µg/ml (1 µl of 50 g/ml antibody was added to 9 µl of liposome solution).

After standing for 30 minutes at room temperature, the antibody was observed by microscopy (Ex: 470-490 Em: 510-550).

As a result, Alexa 488 fluorescence that is caused by an antibody bound to a polypeptide consisting of a sequence comprising a myc tag and a his tag in the C-terminus of an EmrE gene was confirmed as being localized in a liposome membrane. That is, by the above-described method, it was confirmed that a membrane protein was in-vitro synthesized within the liposome, and the membrane protein was incorporated into the liposome membrane.

Next, a DNA comprising an EmrE-myc-his sequence (SEQ ID NO: 1; a sequence comprising a myc tag and a his tag in the C-terminus of an EmrE gene) or a DNA comprising a GUS sequence (SEQ ID NO: 3: negative control comprising a myc sequence and a GUS sequence) was used, and an antibody (anti-Myc tag antibody (mouse IgG1) labeled with Alexa Fluor 488, final concentration 5 µg/ml) diluted with a PBS+1% BSA solution was added to liposomes before and after the expression of proteins (1 µl of 50 g/ml antibody was added to 9 µl of liposome solution) followed by 30 minutes of standing at room temperature for analysis by a cell sorter. The results are shown in FIG. 1. The vertical axis shows the internal volume of liposomes and the horizontal axis shows the fluorescence intensity of Alexa 488. A and B show the results of using the GUS sequence, and C and D show the results of using the EmrE-myc-his sequence. A and C are results of liposomes before the expression of proteins by incubation at 37° C., and B and D are results of liposomes that expressed proteins by an hour incubation at 37° C. As is apparent from FIG. 1, liposomes are prepared under the condition that a single molecule of DNA is enclosed in each liposome, and it was confirmed that a membrane protein was expressed and the membrane protein was able to be detected by an antibody.

Example 2: Confirmation of Function of Membrane Protein Expressed in Unilamellar Liposome 5 nM of a DNA comprising an EmrE-myc-his sequence (SEQ ID NO: 1; a sequence comprising a myc tag and a his tag in the C-terminus of an EmrE gene) or a DNA comprising a GUS sequence (SEQ ID NO: 3: negative control comprising a myc sequence and a GUS sequence) and a PURE system were enclosed within liposomes. The liposomes were incubated for 2 hours at 37° C. to express EmrE-myc-his and GUS-myc. After the preparation of the liposomes, external solution 1 was replaced with external solution 2 containing EtBr 5 µg/ml. Fluorescence was measured every minute, and the intake of EtBr was observed. Subsequently, the same sample was observed with a fluorescence microscope (Ex: 520-550 Em: 580-).

The composition of external solution 1 (that is, the external solution at the time of synthesis of liposomes) is as follows: HEPES-KOH (pH7.6) 100 mM; K-Glu 200 mM; spermidine 4 mM; magnesium acetate 25 mM; CP 40 mM; DTT 2 mM; FD 20 μg/ml; 20 types of amino acids 0.4 mM each; ATP 8 mM; GTP 8 mM; UTP 4 mM; CTP 4 mM.

The composition of external solution 2 (that is, the external solution for making a proton gradient) is as follows: Tris-HCl (pH9.0 or 7.6) 100 mM; K-Glu 200 mM; spermidine 4 mM, magnesium acetate 25 mM; CP 40 mM; DTT 2 mM; FD 20 μg/ml; 20 types of amino acids 0.4 mM each; ATP 8 mM; GTP 8 mM; UTP 4 mM; CTP 4 mM.

The results are shown in FIG. 2. FIG. 2A shows the result of using the DNA comprising the EmrE-myc-his sequence (SEQ ID NO: 1), and FIG. 2B shows the result of using the DNA containing the GUS sequence (SEQ ID NO: 3). In the liposomes that expressed a membrane protein from the EmrE-myc-his sequence, pH-dependent fluorescence intensity was observed. This result verifies that the membrane protein expressed in the liposomes exerted transport ability.

Example 3: Examination on Mg Concentration

DNA5 nM comprising a hemolysin sequence, a halo tag protein and a PURE system were enclosed within liposomes. At this time, liposomes were prepared under 9 conditions of Mg concentration of an intraliposomal solution and an extraliposomal solution, which are 18.88, 23.6, 28.32, 33.04, 37.76, 42.28, 47.2, 51.92, 56.64 mM. After the preparation of liposomes, incubation was performed for 16 hours at 37° C. to express hemolysin. 1 μM of Halo Tag Alexa Fluor 488 ligand was added to the extraliposomal solution to measure the function of expressed alpha hemolysin, and after 3 hours, the amount of fluorescence of Halo Tag Alexa Fluor 488 ligand accumulated within the liposomes was measured. As a result, Halo Tag Alexa Fluor 488 ligand was accumulated the most in liposomes that were prepared by the Mg concentration value of 33.04 mM. Accordingly, it was ascertained that the condition for the detection of activity of hemolysin is preferably 18.88 mM-23.6 mM, more preferably 23.6 mM-28.32 mM, and most preferably 28.32-42.48 mM.

Example 4: Examination on Lipid Component/Composition-1

Instead of the EmrE-myc-his sequence used in Example 1, a sequence encoding hemolysin (SEQ ID NO: 5) was used to express a transporter. Further, a halo tag protein (SEQ ID NO: 7) was used as a factor to which Halo Tag Alexa Fluor 488 ligand, which is the ligand transported by hemolysin, bound. Hemolysin is a membrane protein that creates a pore in a membrane, and hemolysin allows permeation of substances smaller than 3 kDa. Thus, when hemolysin is expressed, a pore is generated in liposomes, and as a result, permeation of Halo Tag Alexa Fluor 488 ligand, which is unable to permeate lipid membranes, is allowed. Halo Tag Alexa Fluor 488 ligand that permeated through the pore binds to the halo tag protein, and as a result, Halo Tag Alexa Fluor 488 ligand that moved into the liposomes accumulate within the liposomes.

As a lipid forming liposomes, a mixture of POPC:Chol=9:1, a mixture of POPC:Chol=7:3, a mixture of POPC:Chol=5:5, and a mixture of POPC:Chol=3:7 were used. Further, POPC is an abbreviation of 1-palmitoyl-2-oleoylphosphatidylcholine, and Chol is an abbreviation of cholesterol. As a result, as shown in FIG. 3, the percentage of exertion of membrane protein activity in liposomes comprising a DNA raised as the ratio of cholesterol increased.

Example 5: Examination on Lipid Component/Composition-2

Next, liposomes were synthesized using various lipids by the same technique as Example 4, and the activity of the expressed membrane protein was compared. The results are shown in FIG. 4.

The vertical axis of FIG. 4 shows the percentage (%) of liposomes that taken in Halo Tag Alexa Fluor 488 ligand with high intensity among all the liposomes when various lipids were used. The lipids that were used are as follows: EggPC is an abbreviation of phosphatidylcholine purified from a hen's egg; POPC is an abbreviation of 1-palmitoyl-2-oleoylphosphatidylcholine; PS is an abbreviation of 1-palmitoyl-2-oleoylphosphoserine; PE is an abbreviation of 1-palmitoyl-2-oleoylphosphoethanolamine; and Chol is an abbreviation of cholesterol. PC mix is an abbreviation of the mixture of 1-palmitoyl-2-oleoylphosphatidylcholine:1-palmitoyl-2-linoleoylphosphatidylcholine:1-stearoyl-2-oleoylphosphatidylcholine:1-stearoyl-2-linoleoylphosphatidylcholine=129:67:48:24 (mass ratio); EggPC/PS/PE is an abbreviation of the mixture of each of them at the ratio of 3:1:1 (mass ratio) in order; EggPC/PS/PE/Chol is an abbreviation of the mixture of each of them at the ratio of 2:1:1:1 (mass ratio) in order; PCmix/PS/PE is an abbreviation of the mixture of each of them at the ratio of 3:1:1 (mass ratio) in order; PCmix/PS/PE/Chol is an abbreviation of the mixture of each of them at the ratio of 2:1:1:1 (mass ratio) in order; POPC/PS/PE is an abbreviation of the mixture of each of them at the ratio of 3:1:1 (mass ratio) in order; and POPC/POPE/POPS/Chol is an abbreviation of the mixture of each of them at the ratio of 2:1:1:1 (mass ratio) in order.

These results ascertained that change in types of phosphatidylcholine and mixture of a plurality of types, and mixture of 1-palmitoyl-2-oleoylphosphoserine and 1-palmitoyl-2-oleoylphosphoethanolamine do not significantly affect the exertion of activity of hemolysin.

Example 6: Concentration of Desired Nucleic Acid

An experiment was performed by using wild type hemolysin (SEQ ID NO: 5) and lethal mutation type hemolysin (SEQ ID NO: 8) and by using the same technique as Example 4. The proportion of wild type to lethal mutation type was set to 1:12, and tenfold or more of lethal mutation type were used. Culturing was performed for 160 minutes at 37° C. to express a membrane protein, and then liposomes that showed transport activity were selected by a cell sorter to determine the percentage of wild type genes and mutated genes included in the liposomes. The result was wild type:mutant type=8:1. This result verifies that hundredfold concentration was performed by the screening/selection of the present invention.

For example, by selecting a liposome showing a desired property and performing mutation induction (for example, random mutation) on the included DNA (or RNA), selection by a cell sorter can be performed by using the group to which mutation is induced as a starting material. By repeating this procedure, concentration of mutated genes having a desired property is possible.

Example 7: Evolutionary Experiment

An evolutionary experiment was performed by using the following procedures.

1) Liposomes are created by a centrifugal sedimentation method.

POPC:Chol=1:1 (wt/wt) was used as the lipid composition. As the composition of the internal solution, the same composition as the cell-free protein synthesis system described in Example 1 (except that the magnesium acetate concentration was changed to 33.04 mM) was used. Further, 100 nM T7 RNA polymerase, 200 mM sucrose, 5 mM β-glucuronidase conjugated halopeptide, 1 mM transferrin conjugated alexa fluor 647, 5 pM DNA (ORF of hemolysin was disposed under the control of a T7 promoter) were used. As the composition of the external solution, a solution containing only a small molecule having the same composition as the cell-free protein synthesis system described in Example 1 (except that the magnesium acetate concentration was changed to 33.04 mM), and 200 mM glucose was used.

2) The external solution was replaced to remove the intraliposomal solution that was mixed into the external solution. Centrifugation was performed for 5 minutes at 6000 G, and after the supernatant was thrown away, the precipitation was resuspend with 300 ml of new extraliposomal solution.

3) A hemolysin protein was synthesized within the liposomes and the hemolysin protein was presented in the lipid membrane. Incubation was performed for 16 hours at 37° C.

4) DNAse was added to degrade the DNA remained in the extraliposomal solution. 4 µl of DNAse (TAKARA recombinant Dnase1) was added to the liposome solution.

5) A fluorescent substrate was added to the external environment. 900 ml of new external solution was added to the liposome solution such that the final volume becomes 1.2 ml. The final concentration was set to 2 nM, and Halo Tag Alexa Fluor 488 ligand was added to the external solution. The fluorescence intensity of liposomes was successively measured with a flow cytometer.

6) The intake of the fluorescent substrate was suspended by competitive inhibitory substrate that is non-fluorescent and that is permeable to lipid bilayer. When appropriate fluorescence intensity was obtained, final concentration 200 nM halo tag biotin ligand was added to the external solution.

7) Concentration of the liposome solution. Centrifugation was performed for 5 minutes at 6000 G, and after the supernatant was thrown away, the precipitation was resuspended with 300 ml of new external solution.

8) 10,000 high-intensity liposomes were sorted from the highest intensity value with a cell sorter (BD, FACS Aria 2).

9) Genetic information was amplified. The sorted liposome solution was purified by using a simplified DNA purification column (QIAGEN MinElute PCR Purification Kit). Subsequently, PCR was performed for 40 cycles (TOYOBO KOD FX Neo was used for the DNA polymerase). PCR was purified by using the DNA purification column again. Subsequently, a gel band was purified by using agarose electrophoresis (life technologies, E-Gel CloneWell SYBR Safe Gel was used). After performing purification by using the DNA purification column again, PCR was performed again for 20 cycles. The PCR product was purified by DNA purification column again for reuse as the DNA stock of the next cycle.

The results are shown in FIG. 5. FIG. 5 is a graph showing the percentage of a group of high-intensity liposomes in which the fluorescence intensity is 260 or over. The upper limit of fluorescence values in which Halo Tag Alexa Fluor 488 ligand adheres to negative-control liposomes not having hemolysin activity is 260. Thus, samples that showed a value over this fluorescence value are samples that showed specific Halo Tag Alexa Fluor 488 ligand intake by hemolysin.

It was shown that the percentage of genes having higher activity increased by repeating the cycle of screening/selection. Further, mutation may be introduced after the isolation of the DNA.

INDUSTRIAL APPLICABILITY

By the use of unilamellar liposomes treated with a nuclease, further highly-efficient screening is enabled, and a gene encoding a membrane protein having a desired function can be selected and obtained.

[Sequence Listing Free Text]
SEQ ID NO: 1: the nucleotide sequence of EmrE-myc-his
SEQ ID NO: 2: the amino acid sequence of EmrE-myc-his
SEQ ID NO: 3: the nucleotide sequence of GUS derived from *Escherichia coli*
SEQ ID NO: 4: the amino acid sequence of GUS derived from *Escherichia coli*
SEQ ID NO: 5: the nucleotide sequence encoding hemolysin derived from *Staphylococcus aureus*
SEQ ID NO: 6: the amino acid sequence of hemolysin derived from *Staphylococcus aureus*
SEQ ID NO: 7: the amino acid sequence of the halo tag protein
SEQ ID NO: 8: the nucleotide sequence encoding the lethal mutation type hemolysin derived from *Staphylococcus aureus*
SEQ ID NO: 9: the amino acid sequence of the lethal mutation type hemolysin derived from *Staphylococcus aureus*

The invention claimed is:

1. A unilamellar liposome enclosing:
   (a) a DNA comprising a promoter sequence, a translational initiation sequence, and a sequence encoding a transporter protein;
   (b) an RNA polymerase;
   (c) a ribonucleotide;
   (d) a cell-free protein synthesis system; and
   (e) a factor that binds to a ligand transported by translated transporter protein,
   wherein the unilamellar liposome is treated with a nuclease, and the nuclease is selected from the group consisting of a ribonuclease and a deoxyribonuclease.

2. The unilamellar liposome of claim 1, wherein the nuclease is a ribonuclease.

3. A library comprising a plurality of unilamellar liposomes of claim 1.

4. The library of claim 3, wherein the nuclease is a ribonuclease.

5. A unilamellar liposome enclosing:
   (a) an RNA comprising a translational initiation sequence, and a sequence encoding a transporter protein;
   (b) a cell-free protein synthesis system; and
   (c) a factor that binds to a ligand transported by translated transporter protein, and
   wherein the unilamellar liposome is treated with a nuclease, and the nuclease is a ribonuclease.

6. A library comprising a plurality of unilamellar liposomes of claim 5.

7. A method of producing the unilamellar liposome of claim 1, comprising:
   (1) preparing a unilamellar liposome enclosing:
      (a) a DNA comprising a promoter sequence, a translational initiation sequence, and a sequence encoding a transporter protein;
      (b) an RNA polymerase;
      (c) a ribonucleotide;
      (d) a cell-free protein synthesis system; and
      (e) a factor that binds to a ligand transported by translated transporter protein, and
   (2) treating the unilamellar liposome prepared in (1) with a nuclease,
   wherein the nuclease is selected from the group consisting of a ribonuclease and a deoxyribonuclease.

8. The method of claim 7, wherein the nuclease is a ribonuclease.

9. A method of producing the unilamellar liposome of claim 5, comprising:
  (1) preparing a unilamellar liposome enclosing:
    (a) an RNA comprising a translational initiation sequence, and a sequence encoding a transporter protein;
    (b) a cell-free protein synthesis system; and
    (c) a factor that binds to a ligand transported by translated transporter protein, and
  (2) treating the unilamellar liposome prepared in (1) with a nuclease,
  wherein the nuclease is a ribonuclease.

10. A screening method using a library of unilamellar liposomes, comprising:
  (i) providing the library of claim 3 or 4;
  (ii) selecting a unilamellar liposome having a desired feature from the library;
  (iii) amplifying a DNA included in the unilamellar liposome to obtain an amplified DNA; and
  (iv) isolating the amplified DNA of (iii).

11. A screening method using a library of unilamellar liposomes, comprising:
  providing the library of claim 6;
  (ii) selecting a unilamellar liposome having a desired feature from the library;
  (iii) generating a DNA by operating a reverse transcriptase on an RNA included in the unilamellar liposome to obtain a generated DNA;
  (iv) amplifying the generated DNA of (iii) to obtain amplified DNA; and
  (v) isolating the amplified DNA of (iv).

* * * * *